(12) United States Patent
Roorda et al.

(10) Patent No.: US 6,804,000 B2
(45) Date of Patent: Oct. 12, 2004

(54) BEAM-STEERING OF MULTI-CHROMATIC LIGHT USING ACOUSTO-OPTICAL DEFLECTORS AND DISPERSION-COMPENSATORY OPTICS

(75) Inventors: Robert Dixon Roorda, Astoria, NY (US); Gero Miesenböck, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 51 days.

(21) Appl. No.: 10/017,912

(22) Filed: Dec. 14, 2001

(65) Prior Publication Data

US 2002/0149769 A1 Oct. 17, 2002

Related U.S. Application Data

(60) Provisional application No. 60/256,221, filed on Dec. 15, 2000.

(51) Int. Cl.[7] .............................. G01J 3/30; G01N 21/64
(52) U.S. Cl. ..................... 356/318; 250/458.1; 359/305; 356/326
(58) Field of Search .................................. 356/318, 326, 356/328, 334; 250/458.1

(56) References Cited

U.S. PATENT DOCUMENTS

| | | |
|---|---|---|
| 4,863,226 A | 9/1989 | Houpt et al. |
| 5,002,348 A | 3/1991 | Wolf |
| 5,034,613 A | 7/1991 | Denk et al. |
| 5,128,798 A | 7/1992 | Bowen et al. |
| 5,691,839 A * | 11/1997 | Kobayashi .................. 359/385 |
| 5,936,764 A * | 8/1999 | Kobayashi .................. 359/385 |
| 6,037,967 A | 3/2000 | Allen et al. |
| 6,449,039 B1 | 9/2002 | Bouzid |
| 6,525,812 B1 * | 2/2003 | Hartmann et al. .......... 356/318 |

OTHER PUBLICATIONS

Denk et al., "Two–Photon Laser Scanning Fluorescence Microscopy," Science, 248:73–6 (Apr. 6, 1990).
Fan et al., "Video–Rate Scanning Two–Photon Excitation Fluorescence Microscopy and Ratio Imaging with Cameleons," Biophysical Journal, 76:2412–20 (May 1999).
Koester et al., "Ca2+ Fluorescence Imaging with Pico– and Femtosecond Two–Photon Excitation: Signal and Photodamage," Biophysical Journal, 77:2226–36 (Oct. 1999).
Mainen et al., "Two–Photon Imaging in Living Brain Slices," Methods, 18:231–9 (1999).
Parthenopoulos et al., "Three–Dimensional Optical Storage Memory," Science, 245:843–5 (Aug. 25, 1989).
Campagnola et al., "High–Resolution Nonlinear Optical Imaging of Live Cells by Second Harmonic Generation," Biophyisical Journal, 77:3341–9 (Dec. 1999).
Denk et al., "Photon Upmanship: Why Multiphoton Imaging Is More than a Gimmick," Neuron, 18:351–7 (Mar. 1997).

(List continued on next page.)

Primary Examiner—F. L. Evans
Assistant Examiner—Kara Geisel
(74) Attorney, Agent, or Firm—Kriegsman & Kriegsman

(57) ABSTRACT

Method and apparatus for steering a beam of light. The method and apparatus are based on the discovery that the spectral dispersion of multi-chromatic light pulses by an acousto-optical deflector can be significantly ameliorated by positioning a dispersive element, such as a prism, along the path of the multi-chromatic light pulses in such a way that the dispersive element disperses the multi-chromatic light pulses in a direction opposite to the spectral dispersion caused by the acousto-optical deflector. The dispersive element may be positioned either before or after the acousto-optical deflector. The method and apparatus are particularly well-suited for use with ultrashort laser pulses in the visible and infrared ranges having a bandwidth of up to about 40 nm. The method and apparatus have applicability in, among other things, multi-photon laser scanning microscopy.

49 Claims, 18 Drawing Sheets

OTHER PUBLICATIONS

Denk et al., "Two–Photon Molecular Excitation in Laser-Scanning MIcroscopy," pp. 445–457 of Handbook of Biological Confocal Microscopy, edited by James B. Pawley, Plenum Press, New York (1995).

Moreaux et al., "Coherent Scattering in Multi–Harmonic Light Microscopy," Biophysical Journal, 80:1568–74 (Mar. 2001).

* cited by examiner

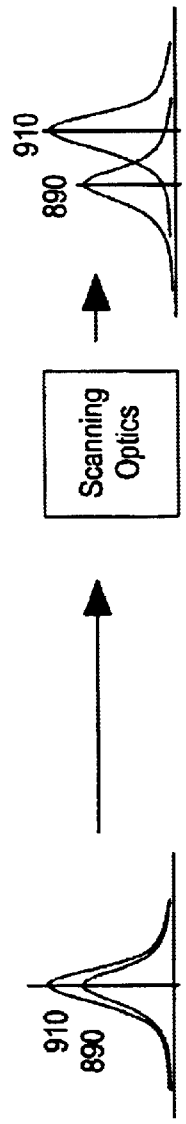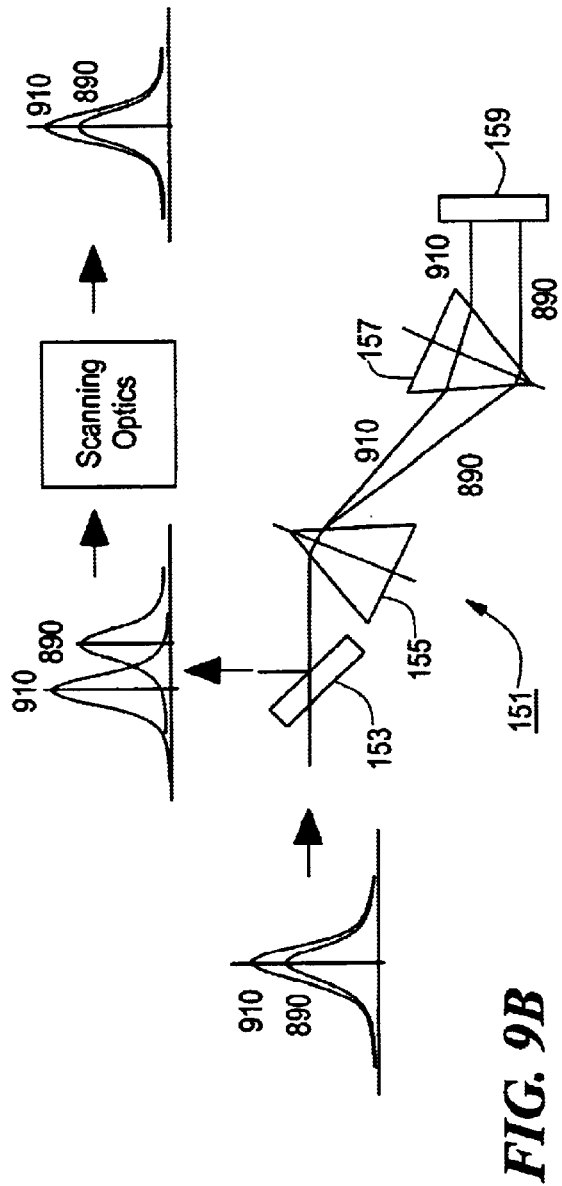
FIG. 9A
FIG. 9B

BEAM-STEERING OF MULTI-CHROMATIC LIGHT USING ACOUSTO-OPTICAL DEFLECTORS AND DISPERSION-COMPENSATORY OPTICS

CROSS-REFERENCE TO RELATED APPLICATIONS

The present application claims the benefit under 35 U.S.C. § 119(e) of U.S. Provisional Patent Application Ser. No. 60/256,221, filed Dec. 15, 2000, the disclosure of which is incorporated herein by reference.

BACKGROUND OF THE INVENTION

The present invention relates generally to optical instrumentation and relates more particularly to the beam-steering of light using acousto-optical deflectors.

Optical instruments have long played an important role in the study of physical and biological phenomena. Light microscopes, in particular, have been used for more than one hundred years to gain insight into the structure of biological media. As can readily be appreciated, achieving high spatial resolution remains one of the foremost objectives of a light microscope. This objective, however, is often hampered by the fact that biological media, by their very nature, are typically highly scattering with respect to light. Consequently, objects located beneath the surface of a biological medium are often difficult to observe with high resolution using light microscopy. As a result, a number of different approaches have been undertaken in an effort to counteract the light scattering effects of biological media.

One such approach is the confocal microscope, an example of which is disclosed in U.S. Pat. No. 4,863,226, inventors Houpt et al., which issued Sep. 5, 1989, and which is incorporated herein by reference. In a confocal microscope, light is brought to focus on or within a sample, and the light emitted from the illuminated sample is then brought to focus on a pinhole positioned in front of a detector, the pinhole being used to prevent light scattered by the sample from reaching the detector. Often in a confocal microscope, the illuminating light is laser light, and a galvanometer or the like is placed along the optical path of the illuminating laser light to create a scanning beam of illuminating laser light. Laser scanning confocal microscopes are often used to create fluorescence images of a sample, with the illuminating laser light being used to excite native and/or extrinsic fluorophores present within the sample, and the non-scattered component of the fluorescent light emitted from said fluorophores being passed through the pinhole and detected by the detector.

One of the problems associated with the use of laser scanning confocal microscopes in fluorescence imaging is that the detected light signal is typically weak. This is because, of all the fluorescence photons generated by the sample, only the non-scattered (i.e., ballistic) photons generated at the illuminating focus (i.e., on-focus) are permitted to pass through the pinhole and are detected by the detector. In other words, not only are the undesirable fluorescence photons generated at loci other than the illuminating focus (i.e., off-focus) excluded from detection but so are the desirable scattered on-focus fluorescence photons, said scattered on-focus fluorescence photons representing a significant portion of the on-focus fluorescence photons.

Another problem associated with the use of laser scanning confocal microscopes in fluorescence imaging is that the intensity of the illuminating light necessary to generate an appreciable detected signal often has the undesirable consequence of adversely affecting the fluorophore (i.e., photobleaching) or adversely affecting the sample through a fluorophore-mediated event (i.e., photodamage). Moreover, because the illuminating light must travel through the sample to the illuminating focus, the above-mentioned effects of photobleaching and photodamage are not confined to the illuminating focus.

One form of laser scanning microscopy that has been devised to address the types of shortcomings discussed above in connection with laser scanning confocal fluorescence microscopy is multi-photon excited fluorescence laser scanning microscopy. In multi-photon excited fluorescence laser scanning microscopy, excitation of a fluorophore is achieved by the simultaneous absorption by the fluorophore of two or more photons of low energy that combine their energies to provide the requisite energy for transition of the fluorophore to its excited state. For example, two photons of lower energy red or infrared light may be used to excite a fluorophore typically excitable by one photon of higher energy ultraviolet light. Because multi-photon absorption requires two or more photons for each excitation, its rate depends on the square of the instantaneous intensity and is, therefore, almost completely confined spatially to the high-intensity region at the focal point of the strongly focused excitation laser.

Consequently, because the requisite energy for excitation is spatially confined to the focal point of the illuminating laser, multi-photon excited fluorescence laser scanning microscopy does not result in off-focus photobleaching or photodamage and does not require the placement of a pinhole in front of the detector, as in confocal fluorescence microscopy, to reject off-focus fluorescence photons. Because such a pinhole is unnecessary in multi-photon excited fluorescence laser scanning microscopy, both scattered and ballistic on-focus fluorescence photons are detected, thereby yielding a stronger signal than if only ballistic on-focus fluorescence photons were detected. Furthermore, because longer wavelength photons typically scatter less in biological media than do shorter wavelength photons, one can achieve improved depth penetration of the media using multi-photon excited fluorescence laser scanning microscopy than using laser scanning confocal fluorescence microscopy.

Additional information relating to multi-photon excited fluorescence laser scanning microscopy is provided in the following published documents, all of which are incorporated herein by reference: U.S. Pat. No. 5,034,613, inventors Denk et al., which issued Jul. 23, 1991; Denk et al., "Two-Photon Laser Scanning Fluorescence Microscopy," *Science*, 248:73–6 (1990); Denk et al., "Photon Upmanship: Why Multiphoton Imaging Is More than a Gimmick," *Neuron*, 18:351–7 (1997); Denk et al., "Two-Photon Molecular Excitation in Laser-Scanning Microscopy," *Handbook of Biological Confocal Microscopy*, pages 445–57, edited by James B. Pawley, Plenum Press, New York (1995); Fan et al., "Video-Rate Scanning Two-Photon Excitation Fluorescence Microscopy and Ratio Imaging with Cameleons," *Biophysical Journal*, 76:2412–20 (1999); Koester et al., "$Ca^{2+}$ Fluorescence Imaging with Pico- and Femtosecond Two-Photon Excitation: Signal and Photodamage," *Biophysical Journal*, 77:2226–36 (1999); Mainen et al., "Two-Photon Imaging in Living Brain Slices," *METHODS: A Companion to Methods in Enzymology*, 18:231–9 (1999); and Parthenopoulos et al., "Three-Dimensional Optical Storage Memory," *Science*, 245:843–5 (1989).

Another form of laser scanning microscopy that has been devised to address the types of shortcomings discussed above in connection with laser scanning confocal fluorescence microscopy is multi-harmonic generation laser scanning microscopy. In one type of multi-harmonic generation laser scanning microscopy, namely, second-harmonic generation laser scanning microscopy, the combined coherent electric fields of two incident photons interact with a dipolar molecule. The incident field is scattered and, in the process, a single photon of exactly half the incident photon wavelength and twice the incident photon energy is formed instantly. This photon is then detected.

As a second-order reaction in the concentration of incident photons, second-harmonic generation laser scanning microscopy possesses the same intrinsic resolving power as two-photon excited fluorescence laser scanning microscopy. In addition, second-harmonic generation laser scanning microscopy, like multi-photon excited fluorescence laser scanning microscopy and unlike laser scanning confocal fluorescence microscopy, does not require the placement of a pinhole in front of the detector. However, unlike multi-photon excited fluorescence laser scanning microscopy, multi-harmonic generation laser scanning microscopy does not require that the object being imaged possess a fluorescent molecule. Instead, multi-harmonic generation laser scanning microscopy merely requires that the object possess the appropriate nonlinear susceptibility. Moreover, as contrasted with multi-photon excited fluorescence laser scanning microscopy, multi-harmonic generation laser scanning microscopy does not involve the absorption and re-emission of energy as only scattering occurs therein and it occurs instantly. Yet another difference between multi-photon excited fluorescence laser scanning microscopy and multi-harmonic generation laser scanning microscopy is that the latter technique requires the use of forward-scattered detection and collection optics since harmonic light propagates only in the forward direction with respect to the exciting light whereas the former technique does not require such forward placement as it relies upon fluorescent light, which is radiated isotropically.

Additional information relating to multi-harmonic generation laser scanning microscopy is provided in the following published documents, both of which are incorporated herein by reference: Campagnola et al., "High-Resolution Nonlinear Optical Imaging of Live Cells by Second Harmonic Generation," *Biophysical Journal*, 77:3341–9 (December 1999); and Moreaux et al., "Coherent Scattering in Multi-Harmonic Light Microscopy," *Biophysical Journal*, 80(3):1568–74 (March 2001).

Acousto-optical deflectors are devices commonly used in the high-speed scanning of light beams. An acousto-optical deflector typically comprises a solid transparent block of homogenous material (e.g., $TeO_2$) onto which one or more rf transducers are bonded. The transducers produce acoustic plane waves that travel through the block of homogeneous material and, thereby, cause a periodic refractive index modulation within the block. Due to the large difference in the respective velocities of sound and light, incident light "sees" this refractive index modulation as a stationary grating and is deflected at a specific angle (the so-called "Bragg angle") with respect to the acoustic wave. As seen by the following equation, the deflection of the incident beam is proportional to the frequency of the acoustic wave (and, thus, the period of the refractive index modulation):

$$\theta = 2 \cdot \theta_{Bragg} = 2 \cdot \frac{\lambda f}{2v} = \frac{\lambda f}{v} \qquad \text{[Eq. 1]}$$

where θ=deflection angle with respect to the incident beam [radians], λ=wavelength of light, f=acoustic wave frequency, and v=velocity of the acoustic wave.

A linear scan of an incident beam by an acousto-optical deflector of the type described above can be produced by ramping the frequency of the rf signal that drives the transducers. Other patterns of beam deflection by an acousto-optical deflector, such as movement of the beam through a set of predefined positions, without an intervening sweep (the so-called "random access" steering), are also possible by applying appropriate command functions to the transducers.

Because acousto-optical deflectors function without moving parts, imaging systems that use acousto-optical deflectors to generate scanning beams possess certain advantages over imaging systems that use movable deflection mirrors to generate scanning beams. More specifically, imaging systems that use acousto-optical deflectors can acquire images at rates from about 30 to nearly 500 Hz and are anticipated to operate at even higher (kHz) repetition rates in random access mode. By contrast, if control of the deflection mirrors involves feedback with a linear command function, the line scan frequency of the deflection mirrors is typically less than 500 Hz. This results in a maximal image acquisition rate of about 1 Hz, a serious limitation to real-time analysis. Higher scan frequencies can be attained when the mirrors are made to be freely oscillating without feedback, but then the mirror deflections become essentially sinusoidal, instead of linear. This has the drawback that only a fraction of the working cycle of a full deflection period (the fraction in which the sine function is approximately linear) is available for data acquisition or that significant post-acquisition processing is required to linearize the image. In addition, the inert mass of a scanning deflection mirror precludes the abrupt accelerations and decelerations that would be required for random access.

Because acousto-optical deflectors of the type described above permit laser scanning at high repetition rates, it would seem to be desirable to utilize such acousto-optical deflectors for laser scanning in multi-photon laser scanning microscopy. However, this has not been feasible because the ultrashort laser pulses that are needed for multi-photon excitation (and for multi-harmonic generation) at biologically tolerable average power levels are not typically monochromatic, but rather, span spectral ranges of up to tens of nanometers. As a result, because the incident ultrashort light pulses on an acousto-optical deflector are typically multi-chromatic, the acousto-optical deflector acts essentially as a diffraction grating for the incident ultrashort light pulses, laterally separating their spectral components (see FIG. 1A). Consequently, pulses with a center wavelength of 900 nm and a bandwidth of about 20 nm, as is typical for the 100 fs pulses used in multi-photon laser scanning microscopy (and in multi-harmonic generation laser scanning microscopy), are dispersed by 0.0729 degrees using an acousto-optical deflector having an acoustic velocity of 4322 m/s and a frequency range centered at 275 MHz. This corresponds to a normalized dispersion of 0.00365 deg/nm. Since a linear scan spans a range of acoustic frequencies, the normalized dispersion usually varies slightly across the scan area, as shown in TABLE I.

TABLE I

| Frequency MHz | Dispersion deg/nm | Dispersion with correction of −0.00365 [deg/nm] deg/nm |
| --- | --- | --- |
| 225 | 0.00299 | −0.00066 |
| 275 | 0.00365 | 0 |
| 325 | 0.00431 | +0.00066 |

In view of the above, it can readily be appreciated that the lateral dispersion of ultrashort laser pulses by an acousto-optical deflector blurs the focus of the exciting beam in the scan direction, with the following two adverse consequences for multi-photon laser scanning microscopy: (i) the spatial resolution in the scan direction is severely compromised; and (ii) the multi-photon excitation efficiency (and the multi-harmonic generation efficiency) is lowered.

SUMMARY OF THE INVENTION

It is an object of the present invention to provide a technique for ameliorating the above-described problem of spectral dispersion of multi-chromatic ultrashort light pulses by acousto-optical deflectors.

Such a technique is provided, in accordance with the teachings of the present invention, by positioning a spectrally dispersive element, such as a prism, along the path of the multi-chromatic ultrashort light pulses in such a way that said dispersive element disperses the multi-chromatic ultrashort light pulses in a direction opposite to the spectral dispersion caused by the acousto-optical deflector. Preferably, the opposing dispersion provided by the spectrally dispersive element equals that provided by the acousto-optical deflector for at least a portion of the dispersed light.

According to one aspect of the invention, there is provided an apparatus for steering a beam of light, said apparatus comprising (a) an acousto-optical deflector; and (b) a spectrally dispersive element, said spectrally dispersive element and said acousto-optical deflector being optically coupled to one another. The spectrally dispersive element may be positioned either in front of said acousto-optical deflector or behind said acousto-optical deflector, said spectrally dispersive element preferably being oriented relative to said acousto-optical deflector so that said spectrally dispersive element disperses multi-chromatic light in a direction opposite to that dispersed by said acousto-optical deflector, said spectrally dispersive element also preferably being constructed to disperse multi-chromatic light in an amount equally opposite to, for at least a portion of said multi-chromatic light, that dispersed by said acousto-optical deflector.

The spectrally dispersive element is preferably a prism but may alternatively be a grating or a second acousto-optical deflector. The apparatus may further comprise one or more mirrors for use in directing the beam along a particular path. More specifically, where the spectrally dispersive element is positioned in front of said acousto-optical deflector, said apparatus preferably further comprises a rotatable mirror and a fixed mirror, said rotatable mirror and said fixed mirror being positioned between spectrally dispersive element and said acousto-optical deflector and serving to redirect the beam, after it passes through the spectrally dispersive element, to the entrance axis of the acousto-optical deflector. The rotatable mirror imparts adjustability for wavelength-dependent variations in the deflection of light by the spectrally dispersive element.

A second set of acousto-optical deflector and spectrally dispersive element can be used, for example, to steer the beam along a second axis perpendicular to the first axis.

The above-described beam steering apparatus can be used to scan a plurality of contiguous locations or can be used to randomly deflect the beam within a plurality of possible locations.

According to another aspect of the invention, there is provided a method of steering a beam of light, said method comprising the steps of (a) providing a beam of light; (b) passing said beam of light through a spectrally dispersive element; and (c) deflecting said beam of light using an acousto-optical deflector. Preferably, the spectrally dispersive element is oriented to disperse multi-chromatic light in a direction opposite to that dispersed by said acousto-optical deflector, and said spectrally dispersive element is preferably constructed to disperse multi-chromatic light, for at least a portion of said multi-chromatic light, in an amount equal to that dispersed by said acousto-optical deflector. The light may be passed through the spectrally dispersive element either before or after being deflected by the acousto-optical deflector.

The beam of light steered by the present method may be either a continuous beam of light or a pulsed beam of light. Preferably, the beam of light is a beam of ultrashort laser light pulses having a pulse duration of less than one picosecond and a bandwidth of no more than about 40 nm. Said light preferably has a wavelength in the range of about 400 to 1000 nm.

The present invention is also directed to an apparatus for spectrally dispersing multi-chromatic light traveling along a first axis, said apparatus comprising (a) a spectrally dispersive element, disposed along said first axis, for dispersing said multi-chromatic light; (b) a pair of mirrors optically coupled to said spectrally dispersive element and positioned thereafter to redirect said dispersed light along said first axis. Preferably, one of said pair of mirrors is a rotatable mirror to adjust for wavelength-dependent variations in the deflection of said dispersed light, and the other of said pair of mirrors is a fixed mirror.

The aforementioned apparatus preferably further comprises means for rotating said rotatable mirror, said rotating means comprising a rotatably mounted arm and a motor for rotating said rotatably mounted arm, said rotatable mirror being fixedly mounted on said rotatably mounted arm. Preferably, said motor is controllable by computer. Said apparatus preferably further comprises a base, said spectrally dispersive element, said pair of mirrors, said rotatably mounted arm and said motor being mounted on said base.

The present invention is additionally directed to a method of imaging a sample using multi-photon excited fluorescence laser scanning microscopy, said method comprising the steps of (a) providing a sample containing fluorescent molecules which radiate photons of a first characteristic energy; (b) producing a scanning beam of ultrashort laser light pulses, said scanning beam being produced by (i) providing a beam of ultrashort laser light pulses comprising photons of a second characteristic energy, wherein said second characteristic energy is less than said first characteristic energy and wherein the simultaneous absorption of a plurality of said photons of said second characteristic energy by said fluorescent molecules causes the fluorescence of said fluorescent molecules, (ii) passing said beam through a spectrally dispersive element, and (iii) deflecting said beam using an acousto-optical deflector, (iv) wherein said spectrally dispersive element is oriented to disperse multi-chromatic light in a direction opposite to that dispersed by said acousto-optical deflector; (c) focusing said scanning beam at a focal point within said sample to produce an illumination intensity sufficiently high only at said focal point to produce molecular excitation and fluorescence of said sample by simultaneous absorption of a plurality of incident photons; (d) detecting the fluorescence produced by said sample; and (e) using the detected fluorescence to form an image of the sample.

Preferably, the spectrally dispersive element used in the aforementioned method is constructed to disperse multi-chromatic light, for at least a portion of said multi-chromatic light, in an amount equal to that dispersed by said acousto-optical deflector. The scanning beam producing step described above preferably further comprises scanning the sample in a direction perpendicular to said first axis, said scanning in a direction perpendicular to said first axis comprising the use of a scanning mirror or a second acousto-optical deflector and a second spectrally dispersive element, said second spectrally dispersive element being oriented relative to said second acousto-optical deflector so as to disperse multi-chromatic light in a direction opposite to that dispersed by said second acousto-optical deflector.

The present invention is further directed to a multi-photon excited fluorescence laser scanning microscope for forming a magnified image of a sample, said sample containing fluorescent molecules which radiate photons of a first characteristic energy, said multi-photon laser scanning microscope comprising (a) means for producing a scanning beam of ultrashort laser light pulses, said scanning beam producing means comprising (i) a laser source for providing a beam of ultrashort laser light pulses comprising photons of a second characteristic energy, wherein said second characteristic energy is less than said first characteristic energy and wherein the simultaneous absorption of a plurality of said photons of said second characteristic energy by said fluorescent molecules causes the fluorescence of said fluorescent molecules, (ii) a first acousto-optical deflector optically coupled to said laser source for scanning said beam along a first axis, (iii) a first spectrally dispersive element optically coupled to said first acousto-optical deflector, said first spectrally dispersive element being oriented relative to said first acousto-optical deflector so as to disperse multi-chromatic light in a direction opposite to that dispersed by said first acousto-optical deflector; (b) means for focusing said scanning beam to a focal point within said sample to produce an illumination intensity sufficiently high only at said focal point to produce molecular excitation and fluorescence of said sample by simultaneous absorption of at least two incident photons; (c) means for detecting the fluorescence produced by said sample; and (d) means for using the detected fluorescence to form a magnified image of the sample.

Preferably, the first spectrally dispersive element of the aforementioned microscope is constructed to disperse multi-chromatic light, for at least a portion of said multi-chromatic light, in an amount equal to that dispersed by said first acousto-optical deflector. The scanning beam producing means of the microscope described above preferably further comprises means for scanning the sample in a direction perpendicular to said first axis, said means for scanning the sample in a direction perpendicular to said first axis comprising a scanning mirror or a second acousto-optical deflector and a second spectrally dispersive element, said second spectrally dispersive element being oriented relative to said second acousto-optical deflector so as to disperse multi-chromatic light in a direction opposite to that dispersed by said second acousto-optical deflector.

The present invention is still further directed to a laser scanning microscope for forming a magnified image of a sample, the sample containing fluorophores, said laser scanning microscope comprising (a) means for producing a scanning beam of light pulses, said scanning beam producing means comprising (i) means for providing a beam of light pulses, said light pulses being of a wavelength suitable to excite said fluorophores, (ii) a first acousto-optical deflector optically coupled to said beam providing means for scanning said beam along a first axis, (iii) a first spectrally dispersive element optically coupled to said first acousto-optical deflector, said first spectrally dispersive element being oriented relative to said first acousto-optical deflector so as to disperse multi-chromatic light in a direction opposite to that dispersed by said first acousto-optical deflector; (b) means for focusing said scanning beam at a focal point within said sample; (c) means for detecting the fluorescence produced by said sample; and (d) means for using the detected fluorescence to form a magnified image of the sample.

The present invention is yet further directed to a method of imaging a sample using multi-harmonic generation laser scanning microscopy, said method comprising the steps of (a) providing a sample, the sample containing molecules having the appropriate nonlinear susceptibility; (b) producing a scanning beam of ultrashort laser light pulses, said scanning beam being produced by (i) providing a beam of ultrashort light pulses comprising photons of a first wavelength capable of interacting with said molecules having the appropriate nonlinear susceptibility to create, by multi-harmonic generation, photons of a second wavelength, (ii) passing said beam through a spectrally dispersive element, and (iii) deflecting said beam using an acousto-optical deflector, (iv) wherein said spectrally dispersive element is oriented to disperse multi-chromatic light in a direction opposite to that dispersed by said acousto-optical deflector; (c) focusing said scanning beam at a focal point within said sample to produce an illumination intensity sufficiently high only at said focal point to generate, by multi-harmonic generation, photons of said second wavelength; (d) detecting the photons of said second wavelength emitted from said sample; and (e) using the detected photons of said second wavelength to form an image of the sample.

Preferably, the spectrally dispersive element used in the aforementioned method is constructed to disperse multi-chromatic light, for at least a portion of said multi-chromatic light, in an amount equal to that dispersed by said acousto-optical deflector. The scanning beam producing step described above preferably further comprises scanning the sample in a direction perpendicular to said first axis, said scanning in a direction perpendicular to said first axis comprising the use of a scanning mirror or a second acousto-optical deflector and a second spectrally dispersive element, said second spectrally dispersive element being oriented relative to said second acousto-optical deflector so as to disperse multi-chromatic light in a direction opposite to that dispersed by said second acousto-optical deflector.

The present invention is further directed to a multi-harmonic generation laser scanning microscope for forming a magnified image of a sample, the sample containing molecules having the appropriate nonlinear susceptibility, said multi-harmonic generation laser scanning microscope comprising (a) means for producing a scanning beam of ultrashort laser light pulses, said scanning beam producing means comprising (i) a laser source for providing a beam of ultrashort light pulses comprising photons of a first wavelength capable of interacting with said molecules having the appropriate nonlinear susceptibility to create, by multi-harmonic generation, photons of a second wavelength, (ii) a first acousto-optical deflector optically coupled to said laser source for scanning said beam along a first axis, (iii) a first spectrally dispersive element optically coupled to said first acousto-optical deflector, said first spectrally dispersive element being oriented relative to said first acousto-optical deflector so as to disperse multi-chromatic light in a direction opposite to that dispersed by said first acousto-optical deflector; (b) means for focusing said scanning beam at a focal point within said sample to produce an illumination intensity sufficiently high only at said focal point to generate, by multi-harmonic generation, photons of said second wavelength; (c) means for detecting the photons of said second wavelength emitted from said sample; and (d) means for using the detected photons of said second wavelength to form an image of the sample.

Preferably, the first spectrally dispersive element of the aforementioned microscope is constructed to disperse multi-chromatic light, for at least a portion of said multi-chromatic light, in an amount equal to that dispersed by said first acousto-optical deflector. The scanning beam producing means of the microscope described above preferably further comprises means for scanning the sample in a direction perpendicular to said first axis, said means for scanning the sample in a direction perpendicular to said first axis comprising a scanning mirror or a second acousto-optical deflector and a second spectrally dispersive element, said second spectrally dispersive element being oriented relative to said second acousto-optical deflector so as to disperse multi-chromatic light in a direction opposite to that dispersed by said second acousto-optical deflector.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which are shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute apart of this specification, illustrate preferred embodiments of the invention and, together with the description, serve to explain the principles of the invention. In the drawings wherein like reference numerals represent like parts:

FIG. 9A is a schematic diagram illustrating the phenomenon of group velocity dispersion in the context of an ultrashort light pulse transmitted through scanning optics;

FIG. 9B is a schematic diagram illustrating an apparatus for compensating for the group velocity dispersion shown in FIG. 9A;

DETAILED DESCRIPTION OF PREFERRED EMBODIMENTS

As noted above, the present invention is based, in large part, on the inventors' unexpected discovery that the spectral dispersion of multi-chromatic ultrashort light pulses by an acousto-optical deflector can be significantly ameliorated by positioning a dispersive element, such as a prism, along the path of the multi-chromatic ultrashort light pulses in such a way that said dispersive element disperses the multi-chromatic ultrashort light pulses in a direction opposite to the spectral dispersion caused by the acousto-optical deflector. As will be seen below, the aforementioned dispersive element may be positioned either before or after the acousto-optical deflector.

Figure 1A:
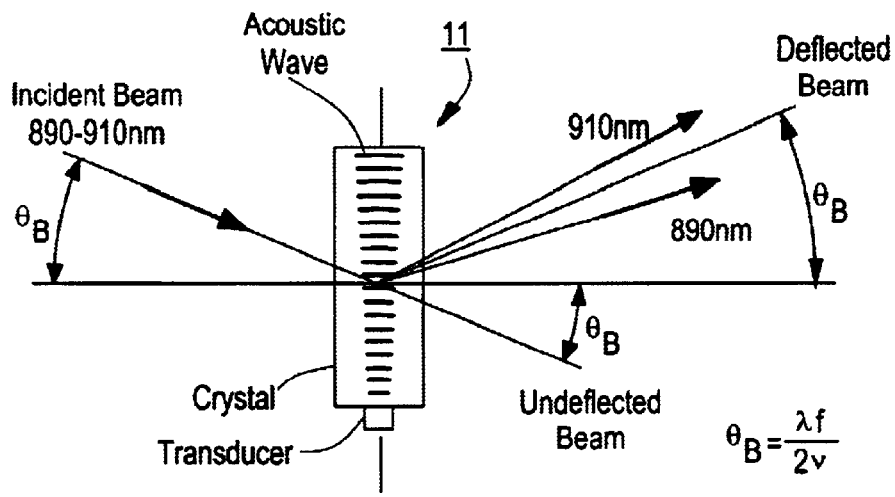
FIG. 1A is a schematic diagram illustrating the problem of unwanted spectral dispersion of a multi-chromatic ultrashort light pulse by a conventional acousto-optical deflector.

The aforementioned principle is aptly illustrated by reference to FIGS. 1A and 1B. As seen in FIG. 1A, when a beam of ultrashort light pulses having a center wavelength of 900 nm and a bandwidth of 20 nm arrives at a conventional acousto-optical deflector 11, a portion of the beam travels undeflected through deflector 11 and another portion of the beam is deflected by deflector 11 at approximately twice the Bragg angle. (Since multi-chromatic light is being used, the Bragg angle referred to herein is to the Bragg angle for the center wavelength of the multi-chromatic light.) The longer wavelengths within the beam are deflected slightly more than twice the Bragg angle, the shorter wavelengths within the beam are deflected slightly less than twice the Bragg angle, and the center wavelength within the beam is deflected at twice the Bragg angle. For the reasons discussed above, such spectral dispersion of the deflected beam is clearly undesirable in many instances.

Figure 1B:
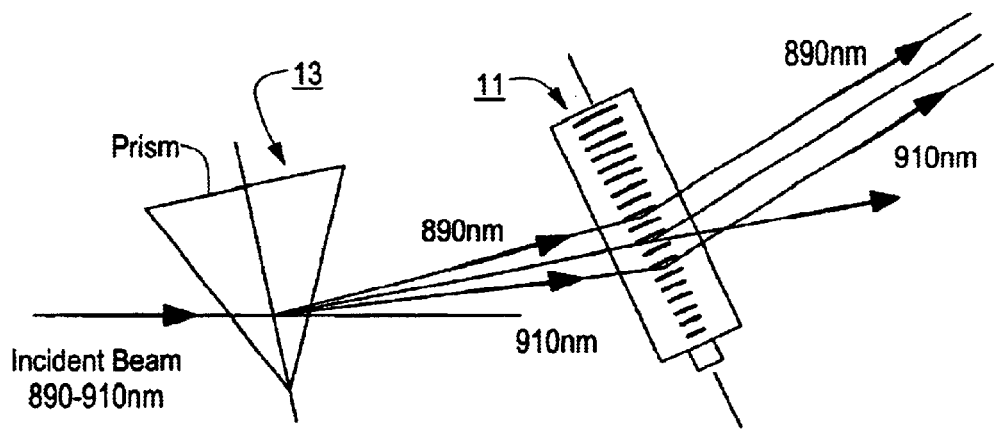
FIG. 1B is a schematic diagram illustrating how a prism may be used in accordance with the teachings of the present invention to compensate for the unwanted spectral dispersion of a multi-chromatic ultrashort light pulse caused by a conventional acousto-optical deflector.

Referring now to FIG. 1B, it can be seen that by positioning a prism 13 along the path of the incident beam of ultrashort light pulses so that prism 13 disperses the incident beam in a direction opposite to the direction of dispersion subsequently caused by deflector 11 and by an amount equal thereto, one can offset, to a substantial extent, the dispersion caused by deflector 11 and can collimate the deflected light. Due to the slight variation of the normalized dispersion across the scan area, the dispersion is fully corrected only at the center frequency of the scan; nevertheless, the overall dispersion can be greatly reduced throughout and is at least 80–90% corrected even at the extremes of the scan area.

As can readily be appreciated, the amount of unwanted dispersion introduced into the deflected beam by the acousto-optical deflector is preferably matched by the amount of oppositely-directed dispersion provided by the prism or other dispersive element. Therefore, to assist one in selecting an appropriate prism, the following relationship governing the deflection of a beam of light by a prism is provided:

$$\delta = 2 \cdot \sin^{-1}\left[n(\lambda) \cdot \sin\left(\frac{\phi}{2}\right)\right] - \phi \qquad \text{[Eq. 2]}$$

where $\delta$=the deflection of the beam, $n(\lambda)$=the index of refraction of the prism material at wavelength $\lambda$, and $\phi$=the apex angle of the prism. From this, the normalized dispersion is represented as follows:

$$\text{normalized dispersion} \cong \frac{\delta(\lambda - \Delta\lambda) + \delta(\lambda + \Delta\lambda)}{2\Delta\lambda} \qquad \text{[Eq. 3]}$$

Different types of prism materials have different dispersive properties determined by their refractive index, $n(\lambda)$. Table II, generated using Equations 2 and 3, tabulates the dispersion of a light pulse with a center wavelength of 900 nm and a bandwidth of 20 nm by a prism made of SF10 glass (Schott Glass Technologies) as a function of its apex angle. For such a light pulse, it can be seen that a prism with an apex angle of 58.4 degrees matches the dispersion of 0.00365 deg/nm caused by an acousto-optical deflector operating at 275 MHz and having an acoustic velocity of 4322 m/s.

TABLE II

| Prism Apex Angle (deg) | Deflection at 890 nm n = 1.707374 (deg) | Deflection at 910 nm n = 1.706651 (deg) | Deflection at 900 nm n = 1.707007 (deg) | Deflection Difference 890–910 nm (deg/20 nm) | Normalized Dispersion at 900 nm (deg/nm) |
|---|---|---|---|---|---|
| 40 | 31.46 | 31.42 | 31.44 | −0.0349 | −0.0017451 |
| 41 | 32.44 | 32.41 | 32.43 | −0.0362 | −0.0018097 |
| 42 | 33.45 | 33.41 | 33.43 | −0.0375 | −0.0018766 |
| 43 | 34.48 | 34.44 | 34.46 | −0.0389 | −0.0019461 |
| 44 | 35.52 | 35.48 | 35.50 | −0.0404 | −0.0020184 |
| 45 | 36.59 | 36.55 | 36.57 | −0.0419 | −0.0020937 |
| 46 | 37.69 | 37.65 | 37.67 | −0.0434 | −0.0021724 |
| 47 | 38.81 | 38.77 | 38.79 | −0.0451 | −0.0022548 |
| 48 | 39.97 | 39.92 | 39.94 | −0.0468 | −0.0023412 |

TABLE II-continued

| Prism Apex Angle (deg) | Deflection at 890 nm n = 1.707374 (deg) | Deflection at 910 nm n = 1.706651 (deg) | Deflection at 900 nm n = 1.707007 (deg) | Deflection Difference 890–910 nm (deg/20 nm) | Normalized Dispersion at 900 nm (deg/nm) |
|---|---|---|---|---|---|
| 49 | 41.15 | 41.10 | 41.13 | −0.0486 | −0.0024321 |
| 50 | 42.37 | 42.32 | 42.34 | −0.0506 | −0.0025281 |
| 51 | 43.62 | 43.57 | 43.60 | −0.0526 | −0.0026296 |
| 52 | 44.91 | 44.86 | 44.89 | −0.0548 | −0.0027375 |
| 53 | 46.25 | 46.19 | 46.22 | −0.0571 | −0.0028525 |
| 54 | 47.63 | 47.57 | 47.60 | −0.0595 | −0.0029757 |
| 55 | 49.07 | 49.01 | 49.04 | −0.0622 | −0.0031082 |
| 56 | 50.56 | 50.49 | 50.53 | −0.0650 | −0.0032514 |
| 57 | 52.11 | 52.04 | 52.08 | −0.0681 | −0.0034071 |
| 58 | 53.74 | 53.67 | 53.70 | −0.0716 | −0.0035776 |
| 59 | 55.44 | 55.36 | 55.40 | −0.0753 | −0.0037657 |
| 60 | 57.23 | 57.15 | 57.19 | −0.0795 | −0.0039749 |
| 61 | 59.12 | 59.04 | 59.08 | −0.0842 | −0.0042100 |
| 62 | 61.13 | 61.04 | 61.09 | −0.0896 | −0.0044776 |
| 63 | 63.28 | 63.18 | 63.23 | −0.0957 | −0.0047864 |
| 58.4 | 54.41 | 54.33 | 54.37 | −0.0730 | −0.0036506 |

Figure 2:
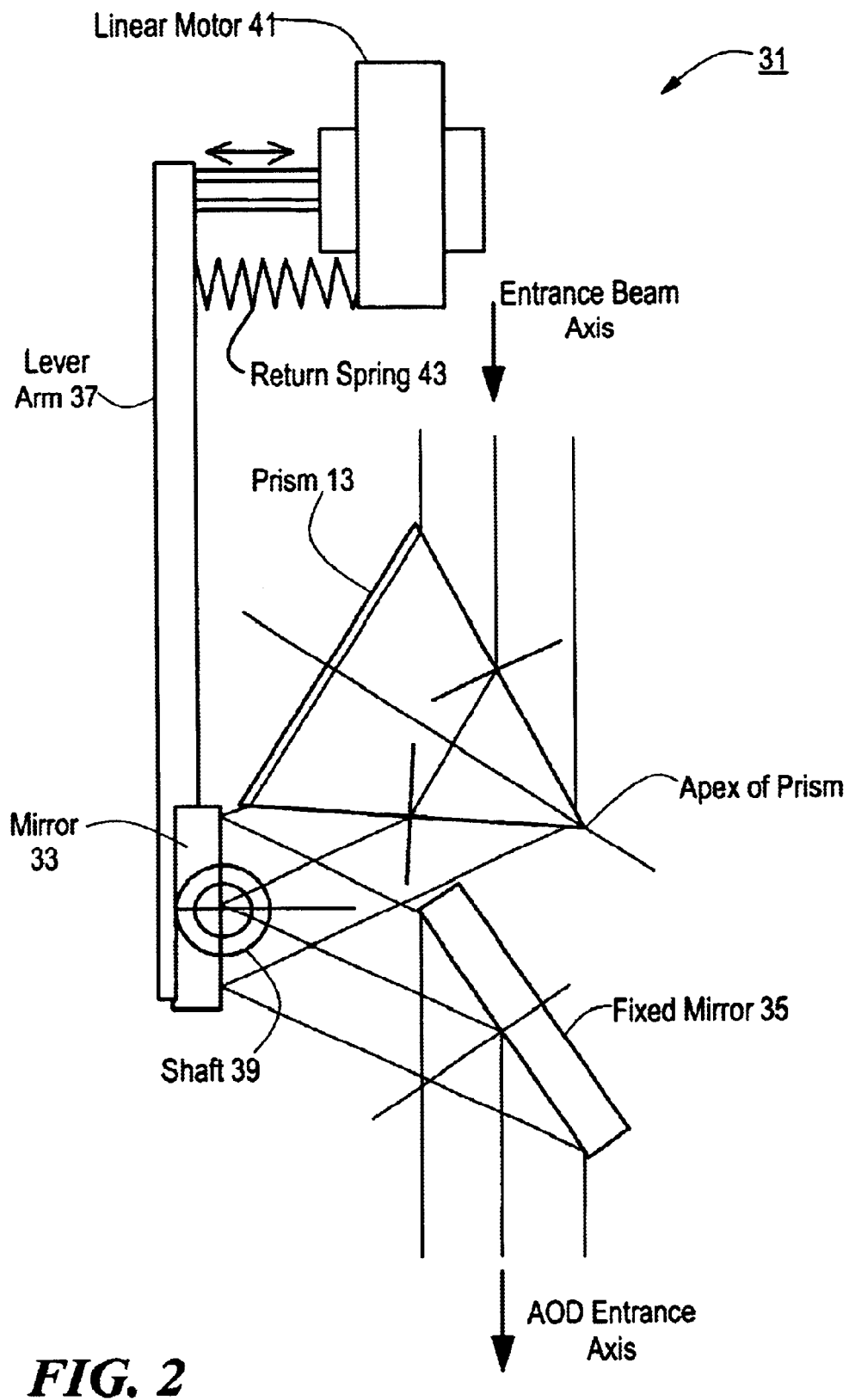
FIG. 2 is a schematic diagram of a first embodiment of an apparatus adapted for compensating for the spectral dispersion of multi-chromatic light by an acousto-optical deflector, said apparatus being constructed according to the teachings of the present invention.
Figure 3:
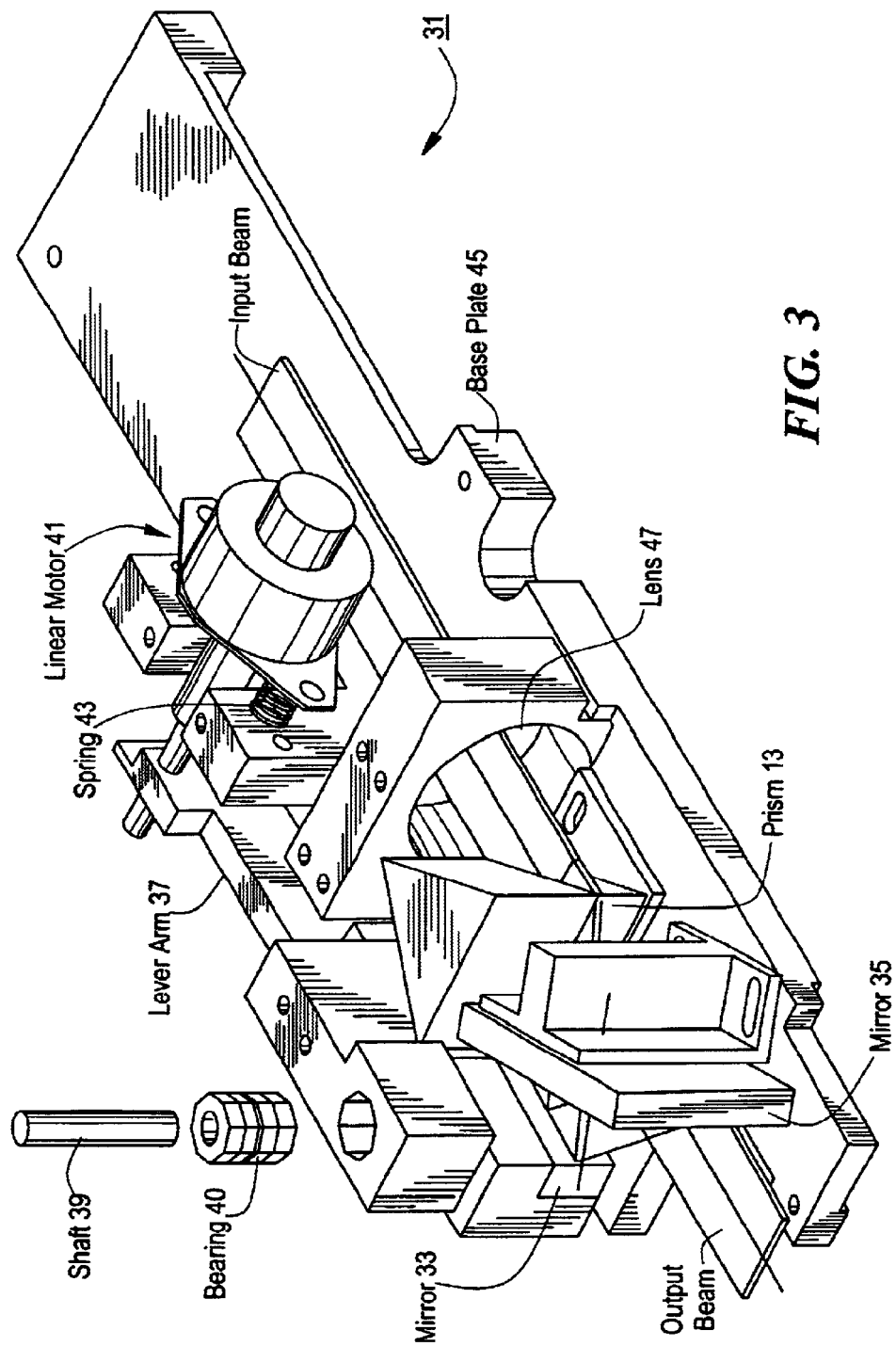
FIG. 3 is a partially exploded perspective view of an implementation of the apparatus of FIG. 2.

Referring now to FIGS. 2 and 3, there are shown schematic and partially exploded perspective views, respectively, of a first embodiment of an apparatus adapted for compensating for the spectral dispersion of multi-chromatic light by an acousto-optical deflector, said apparatus being constructed according to the teachings of the present invention and being represented generally by reference numeral 31.

Apparatus 31, which is particularly well-suited for placement along a beam path in front of an acousto-optical deflector, comprises a prism 13 and a pair of planar mirrors 33 and 35. Mirrors 33 and 35 are positioned after prism 13 and are used to restore the prism-dispersed beam to its original path. (If restoration of the dispersed beam to its original path is not necessary, mirrors 33 and 35 may be omitted.) Mirror 33 is fixedly mounted on a lever arm 37, lever arm 37 being rotably mounted on a shaft 39 disposed within a bearing 40 (bearing 40 shown in FIG. 3 only). A linear 41 and a return spring 43 are mechanically coupled to lever arm 37 (above the plane of the input beam) and are used to rotate arm 37 and mirror 33 about shaft 39. Mirror 35 is kept stationary. The rotational adjustability of mirror 33 enables apparatus 31 to function over a broad spectral range by compensating for the wavelength-dependent variation in the deflection of the beam by prism 13 in such a way as to enable the center wavelength of the dispersed beam to be restored to its original path. To illustrate the wavelength-dependent variation in the deflection of the center wavelength by a prism, TABLE III lists several wavelengths commonly used in laser-scanning microscopy, the indices of refraction of SF10 glass at these wavelengths, and the deflection angles produced at these wavelengths by an SF10 glass prism with an apex angle of 58.4 degrees.

TABLE III

| Wavelength (nm) | Index of Refraction | Deflection Angle (deg.) |
|---|---|---|
| 456 | 1.75497 | 59.38 |
| 488 | 1.74602 | 58.42 |
| 514 | 1.74019 | 57.80 |
| 543 | 1.73481 | 57.23 |
| 633 | 1.72307 | 56.01 |

TABLE III-continued

| Wavelength (nm) | Index of Refraction | Deflection Angle (deg.) |
|---|---|---|
| 800 | 1.71124 | 54.80 |
| 850 | 1.70895 | 54.57 |
| 900 | 1.70701 | 54.37 |

Preferably, the rotation of mirror 33 by motor 41 is placed under software control so that exact beam alignment is performed automatically for each selected wavelength.

As seen in FIG. 3, apparatus 31 further comprises a base plate 45, upon which the foregoing components of apparatus 31 are directly or indirectly mounted.

As can readily be appreciated, prism 13 must be positioned to lie in the plane of the scan that will thereafter be performed by the acousto-optical deflector (or in its optically equivalent plane if there are intermediate mirrors). Such an arrangement ensures that the dispersion introduced by prism 13 is in a direction opposite to that introduced by the acousto-optical deflector. Light passing through prism 13 must be collimated within said plane (hence lens 47 shown in FIG. 3) but may be slightly convergent or divergent in the perpendicular direction. These requirements are similar to the input requirements for an acousto-optical deflector. Preferably, the beam should be P-polarized with respect to its intersection with the prism surface and should enter and leave the prism at or near the Brewster angle (with respect to the surface normal) calculated for the designated wavelength and prism glass. Under these conditions, reflections from the prism surfaces are minimized and the best efficiency is achieved. The prism is preferably provided with antireflective coatings that are selected for these incidence angles and the relevant wavelengths.

Figure 4:
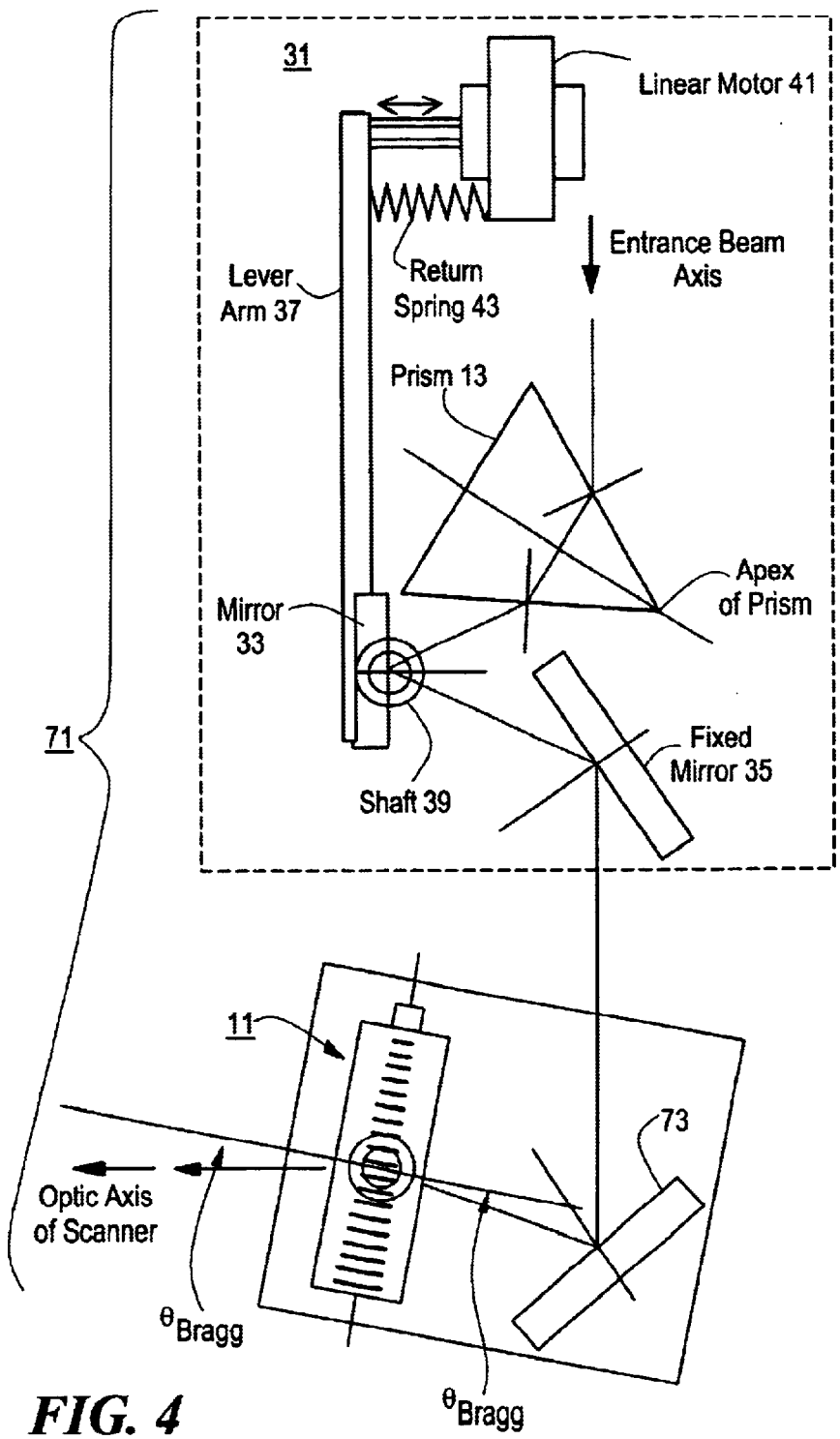
FIG. 4 is a schematic diagram of a first embodiment of an apparatus for steering a beam of light, said apparatus being constructed according to the teachings of the present invention.

Referring now to FIG. 4, there is shown a schematic diagram of a first embodiment of an apparatus for steering a beam of light, said apparatus being constructed according to the teachings of the present invention and being represented generally by reference numeral 71.

Apparatus 71 comprises a combination of apparatus 31 and acousto-optical deflector 11. Deflector 11 is positioned along the path of the beam outputted by apparatus 31, and apparatus and deflector 11 are oriented relative to one another so that apparatus 31 compensates for the spectral dispersion of multi-chromatic light subsequently caused by deflector 11. A mirror 73 is positioned between apparatus 31 and deflector 11 to direct the outputted beam from apparatus 31 to deflector 11, and mirror 73 and deflector 11 are rotatable as a unit to keep the exit beam aligned to the optic axis for any Bragg angle.

Apparatus 71 is most compatible with light in the visible to infrared range (i.e., about 400 to 1000 nm) wherein the bandwidth is less than or equal to about 40 nm. The aforementioned upper wavelength limit stems from the fact that, at said upper wavelengths, the corrective prism is unable to introduce sufficient dispersion to fully offset that introduced by the acousto-optical deflector. The lower wavelength limit is attributable to the reduced transmission of many optical components at said short wavelengths.

Apparatus 71 is suitable for use in a variety of applications that involve beam scanning, such as in a multi-harmonic generation laser scanning microscope, a single-photon excited fluorescence laser scanning microscope and a multi-photon excited fluorescence laser scanning microscope (e.g., for analyzing or perturbing fast physiological processes in cultured cells and tissues, in explanted tissues, in exposed tissues and in intact organisms). When apparatus 71 is used in multi-harmonic generation laser scanning microscopy or in multi-photon excited fluorescence laser scanning microscopy, light pulses in either the picosecond or femtosecond regimes may be used. Although picosecond pulses are essentially monochromatic (bandwidth≦1 nm) and, thus, suffer less lateral dispersion by the acousto-optical deflector than do femtosecond pulses, femtosecond pulses are preferred due to their higher peak power and, thus, higher two-photon excitation efficiency and multi-harmonic generation efficiency. As can readily be appreciated, apparatus 71 could be used in a laser scanning microscope that has both single-photon confocal and multi-photon non-confocal modes, as well as a multi-harmonic generation mode.

Figure 5A:
FIGS. 5A and 5B are two-photon laser scanning microscopic images of a 2.5 $\mu$m spherical object using 100 fs pulses at 900 nm, without and with, respectively, the addition of the dispersion-compensating apparatus of FIG. 2.
Figure 5B:
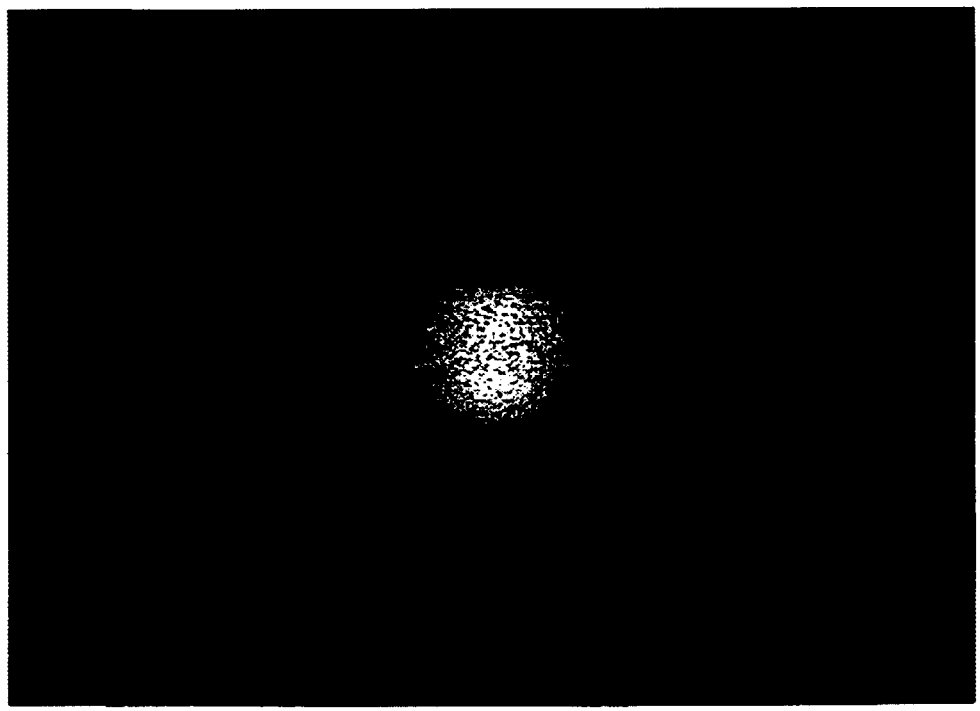

The benefits of using the dispersion-correcting optics of the present invention in multi-photon laser scanning microscopy can readily be seen by a comparison of FIG. 5A to FIG. 5B. In FIG. 5A, there is shown a two-photon image of a 2.5 $\mu$m spherical InSpeck Bead (Molecular Probes) obtained using 100 fs pulses at 900 nm. In FIG. 5B, the same object is imaged under the same conditions, except that the dispersion-compensating optics of the present invention are additionally employed. As can be seen, the resolution and signal-to-noise ratio are appreciably improved with the addition of the dispersion-compensating optics of the present invention.

Apparatus 71 is also well-suited for many other applications in which light beams must be steered rapidly or in patterns that do not conform to linear or sinusoidal scans, such as in photochemistry in vitro and in vivo (e.g., to activate photosensitive molecules capable of effecting changes in cellular microenvironments), in materials processing (e.g., etching, pattern reproduction), in cell or tissue ablation, and in optical memory devices.

As noted above, the present invention achieves complete dispersion correction at only one scan position, typically chosen to lie in the center of the scan area. To achieve complete dispersion correction across the entire scan area, optics whose magnification is proportional to wavelength would have to be placed after the acousto-optical deflector. Thus, the angular deflection of longer wavelengths would be proportionally decreased and that of shorter wavelengths would be proportionally increased. A further requirement would be that the system remain par-focal for the entire pulse bandwidth (i.e., beam collimation is not wavelength dependent).

Figure 6:
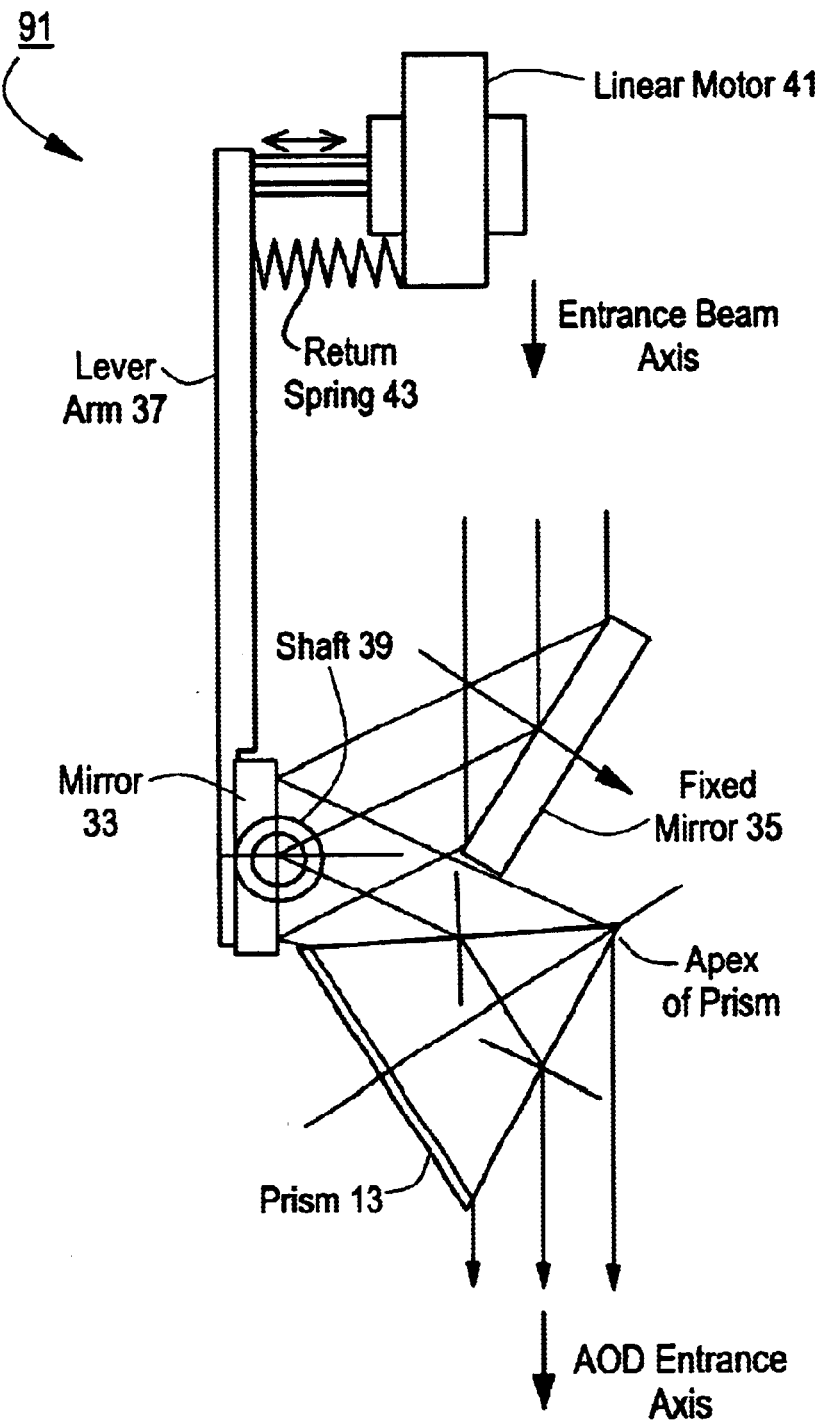
FIG. 6 is a schematic diagram of a second embodiment of an apparatus for compensating for the spectral dispersion of multi-chromatic light by an acousto-optical deflector, said apparatus being constructed according to the teachings of the present invention.

Referring now to FIG. 6, there is shown a schematic diagram of a second embodiment of an apparatus for compensating for the spectral dispersion of multi-chromatic light by an acousto-optical deflector, said apparatus being constructed according to the teachings of the present invention and being represented generally by reference numeral 91.

Apparatus 91 is similar in many respects to apparatus 31, the principal difference between the two apparatuses being that the positions of prism 13 and fixed mirror 35 are reversed in apparatus 91, as compared to apparatus 31.

Figure 7:
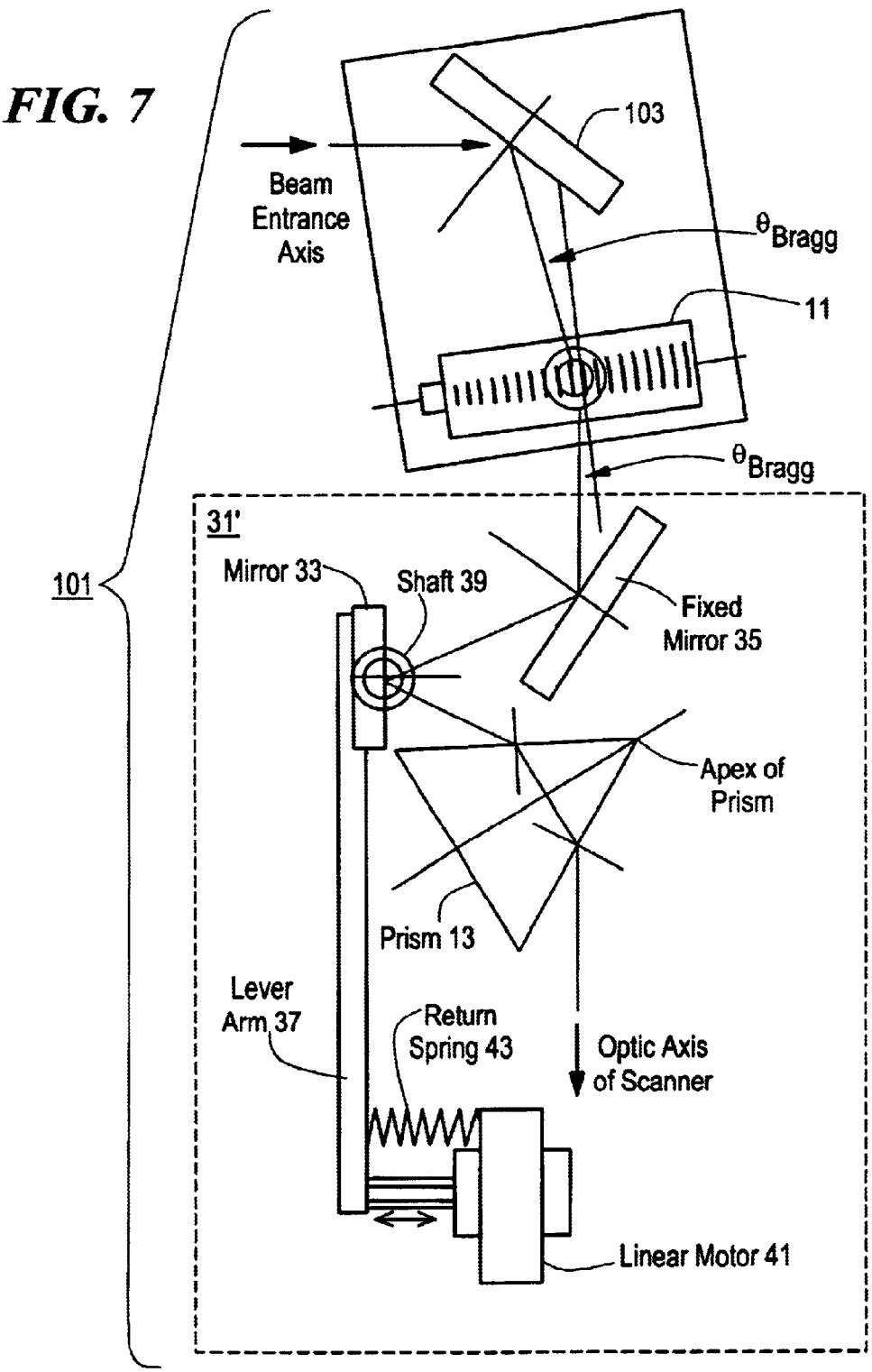
FIG. 7 is a schematic diagram of a second embodiment of an apparatus for steering a beam of light, said apparatus being constructed according to the teachings of the present invention.

Referring now to FIG. 7, there is shown a schematic diagram of a second embodiment of an apparatus for steering a beam of light, said apparatus being constructed according to the teachings of the present invention and being represented generally by reference numeral 101.

Apparatus 101 is similar to apparatus 71, apparatus 101 comprising a combination of acousto-optical deflector 11 and a mirror image apparatus 31' of apparatus 31. Apparatus 31' and deflector 11 are oriented relative to one another so that apparatus 31' compensates for the spectral dispersion of multi-chromatic light previously caused by deflector 11. A mirror 103 is positioned in front of deflector 11 to direct an input beam to deflector 11, and mirror 103 and deflector 11 are rotatable as a unit to keep the exit beam aligned to the optic axis for any Bragg angle.

In general, it is preferable to position the dispersion-compensating apparatus before the acousto-optical deflector, as in apparatus 71, instead of after the acousto-optical deflector, as in apparatus 101. This is because the former arrangement places the dispersion-compensating optics at a location where the exciting beam is stationary and collimated in the scan direction. Such an arrangement also ensures that the alignment of the corrective optics is independent of any other adjustments that may be needed, such as matching the Bragg conditions of the acousto-optical deflector, collimation adjustments, astigmatism, etc. Placing the acousto-optical deflector before the dispersion-compensating apparatus also requires that the beam deflections by the acousto-optical deflector be small.

Figure 8:
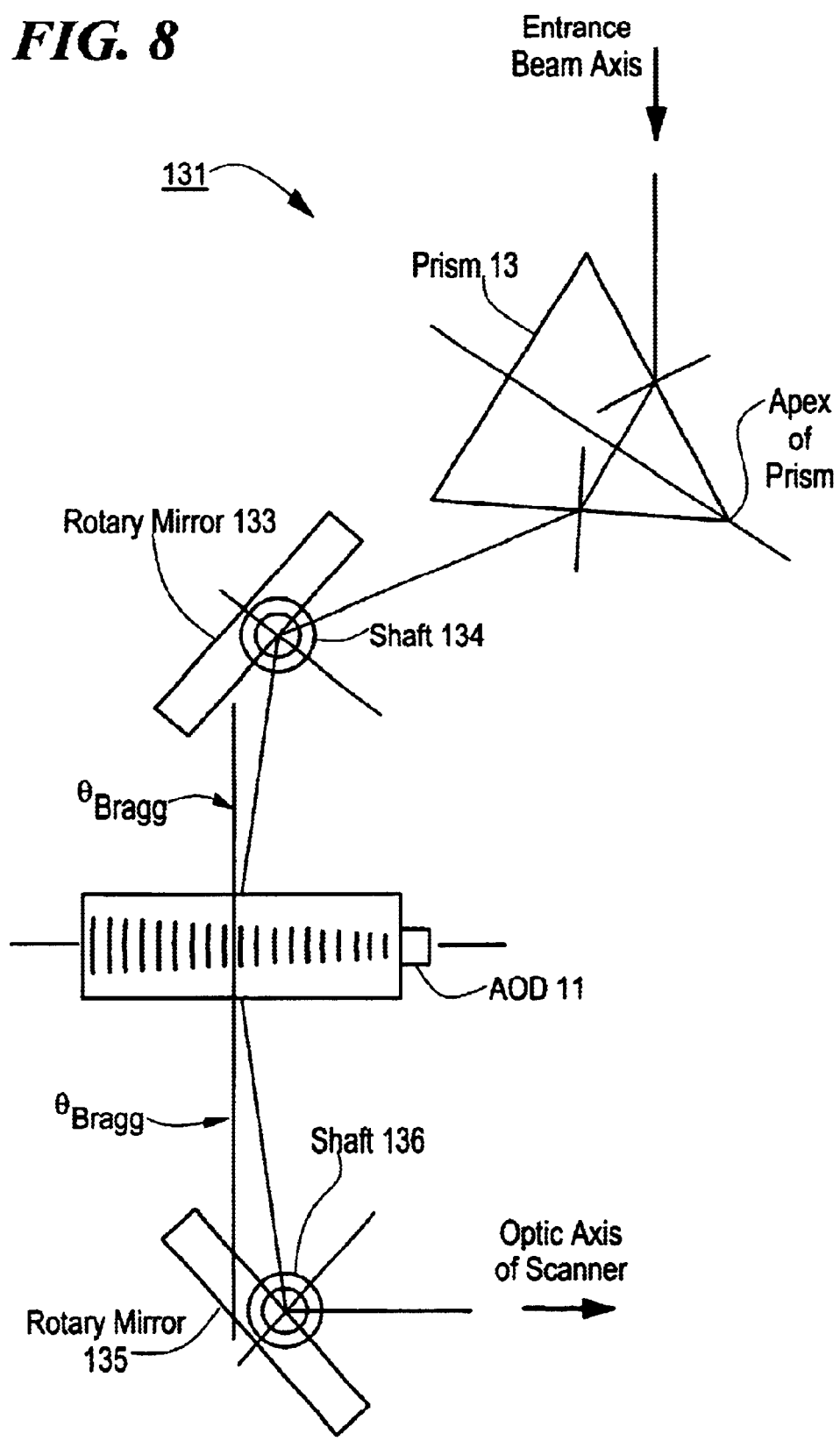
FIG. 8 is a schematic diagram of a third embodiment of an apparatus for steering a beam of light, said apparatus being constructed according to the teachings of the present invention.

A schematic diagram of a third embodiment of a beam-steering apparatus is shown in FIG. 8 and is represented generally by reference numeral 131. As can be seen, apparatus 131 comprises prism 13, acousto-optical deflector 11 positioned after prism 13, a first mirror 133 positioned between prism 13 and deflector 11 and rotatable about a shaft 134, and a second mirror 135 positioned after deflector 11 and rotatable about a shaft 136. Preferably, rotation of rotatable mirrors 133 and 135 is controlled by computer. In this arrangement, the rotational adjustment for aligning the center wavelength of the beam exiting the prism, and the rotational adjustment for matching the Bragg angle conditions at the acousto-optical deflector are combined, and the deflector remains stationary.

The propagation of broad-band pulses through dispersive media, such as those found in the various beam-steering apparatuses described above, typically results in the shorter wavelength components of the pulses being delayed relative to the longer wavelength components of the pulses and, hence, in the temporal spreading of the pulses (see FIG. 9A). This pulse-spreading phenomenon is typically referred to in the art as group velocity dispersion and is clearly undesirable for many applications, such as multi-photon laser scanning microscopy, wherein short pulse lengths and high peak powers are necessary. Consequently, it may be desirable to precede the beam-steering apparatuses of the present invention with an apparatus for temporally advancing the shorter wavelength components relative to the longer wavelength components and thereby compensating for group velocity dispersion. An illustrative group velocity dispersion compensation apparatus is schematically shown in FIG. 9B and is represented by reference numeral 151. Apparatus 151 comprises a mirror 153, a pair of prisms 155 and 157, and a mirror 159. In use, a light pulse travels past mirror 153, is transmitted through prisms 155 and 157, is reflected off mirror 159, is transmitted back through prisms 157 and 155, and is reflected off mirror 153.

The beam-steering apparatuses described above may be used in multi-photon laser scanning microscopy, in multi-harmonic generation laser scanning microscopy and in other applications to scan in the "fast" or x-axis. In such applications, a conventional galvanometric mirror or the like may also be used to scan in the "slow" or y-axis. At 30 Hz (video rate), such a beam typically sweeps an area of 512 pixels in the fast axis and 480 pixels in the slow axis. In this type of "single acousto-optical deflector" arrangement, higher scan rates (up to or exceeding 480 Hz) are possible by reducing the scan area such that the beam visits each pixel more frequently.

Figure 10:
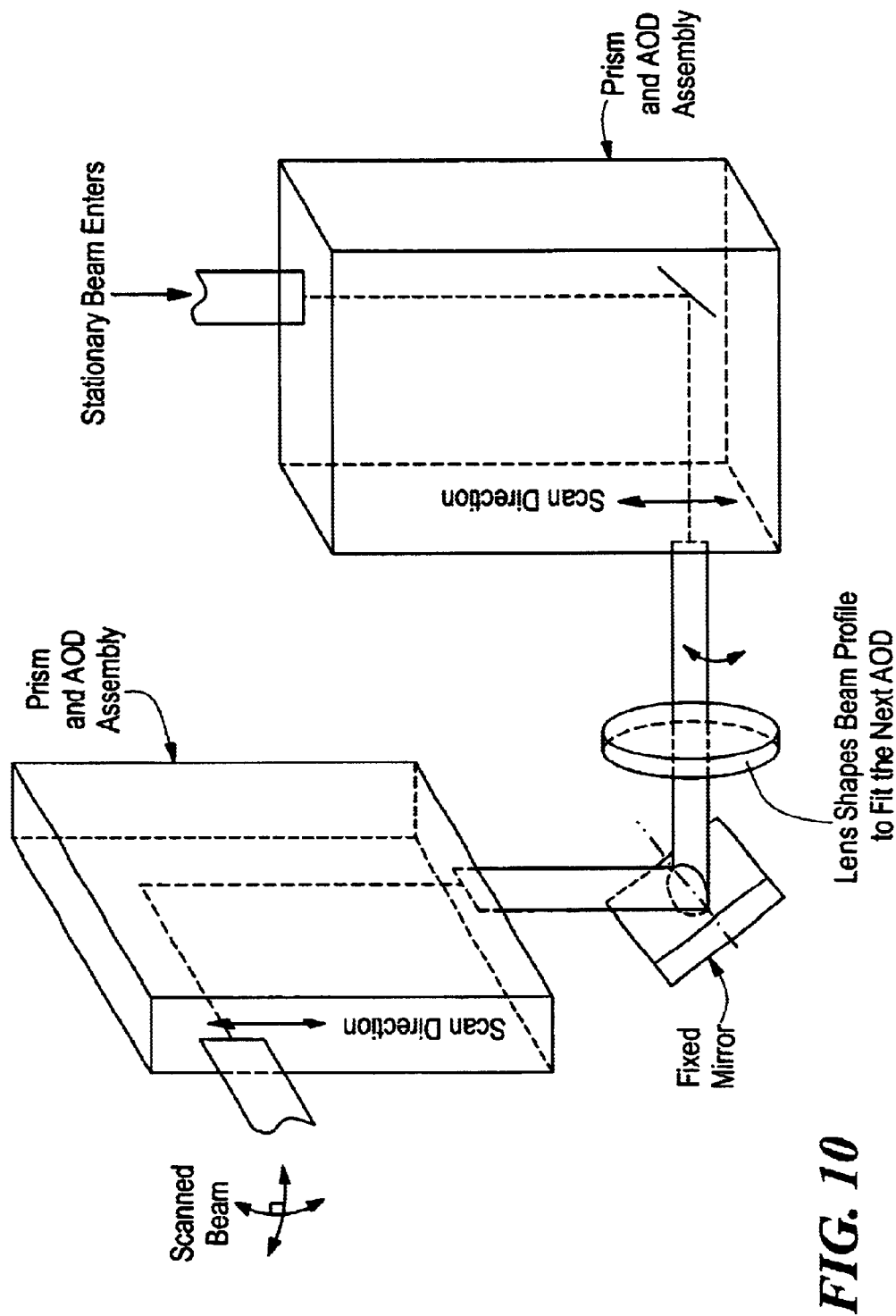
FIG. 10 is a schematic diagram illustrating a fourth embodiment of an apparatus for steering a beam of light, said apparatus being constructed according to the teachings of the present invention.
Figure 12A:
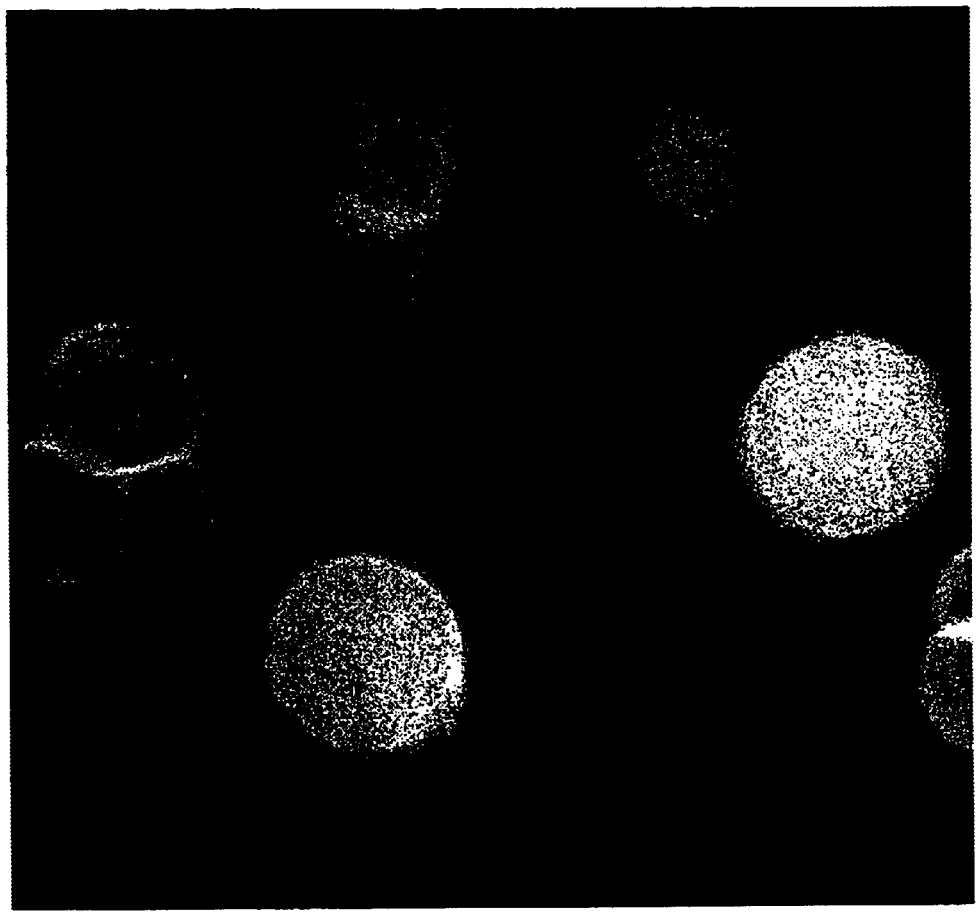
FIGS. 12A through 12D are images of fluorescent pollen grains obtained using the laser scanning microscope of FIG. 11 in a two-photon excited fluorescence mode, using 100 fs pulses centered at 900 nm for illumination and image acquisition rates of (A) 30 Hz; (B) 120 Hz; (C) 240 Hz; and (D) 480 Hz, respectively (scale bar=20 $\mu$m)
Figure 12B:
Figure 12C:
Figure 12D:

An alternative arrangement, shown in FIG. 10, uses acousto-optical deflectors and dispersion-compensating optics to scan in both the x- and y-axes. Even if efficient excitation requires a minimum dwell time of the exciting beam on each pixel (such that acquisition of full-sized images at, for example, 480 Hz would lead to a prohibitively low signal-to-noise ratio), such a "dual acousto-optical deflector" arrangement would have utility in the following two areas: (1) in flexible imaging area selection at high scan rates; and (2) in random access. With respect to the former, as can be appreciated, imaging areas with a "single acousto-optical deflector" is constrained by the inert mass of the galvanometric mirror scanning the slow axis. At high scan speeds, the amplitude of mirror excursions has to be kept small, with a consequent reduction of the scan range in the y-axis. This constrains the aspect ratio of the scanned area to an oblong rectangular format (see FIGS. 12A through 12D wherein the use of a scan mirror in the slow axis constrains the aspect ratio of the images in FIGS. 12C and 12D obtained at high image acquisition frequencies). A "dual acousto-optical deflector" arrangement is not subject to this limitation.

The "dual acousto-optical deflector" arrangement described above is not only capable of producing fast linear scans in both the x and y axes, it also allows the exciting light beam to move virtually instantaneously from any given pixel to any other pixel within the imaging area. The exciting light beam can, therefore, visit any predefined set of pixels (which need not be contiguous) in any temporal sequence and at very short intervals, the deflectors effectively shuttering the beam while in transit. As can readily be appreciated, there are many applications where it would be desirable to interrogate defined areas of interest at very high (i.e., kHz) repetition rates, rather than to acquire full-sized images (which will contain much useless information) at much lower rates. Random access achieves this objective.

Figure 11:
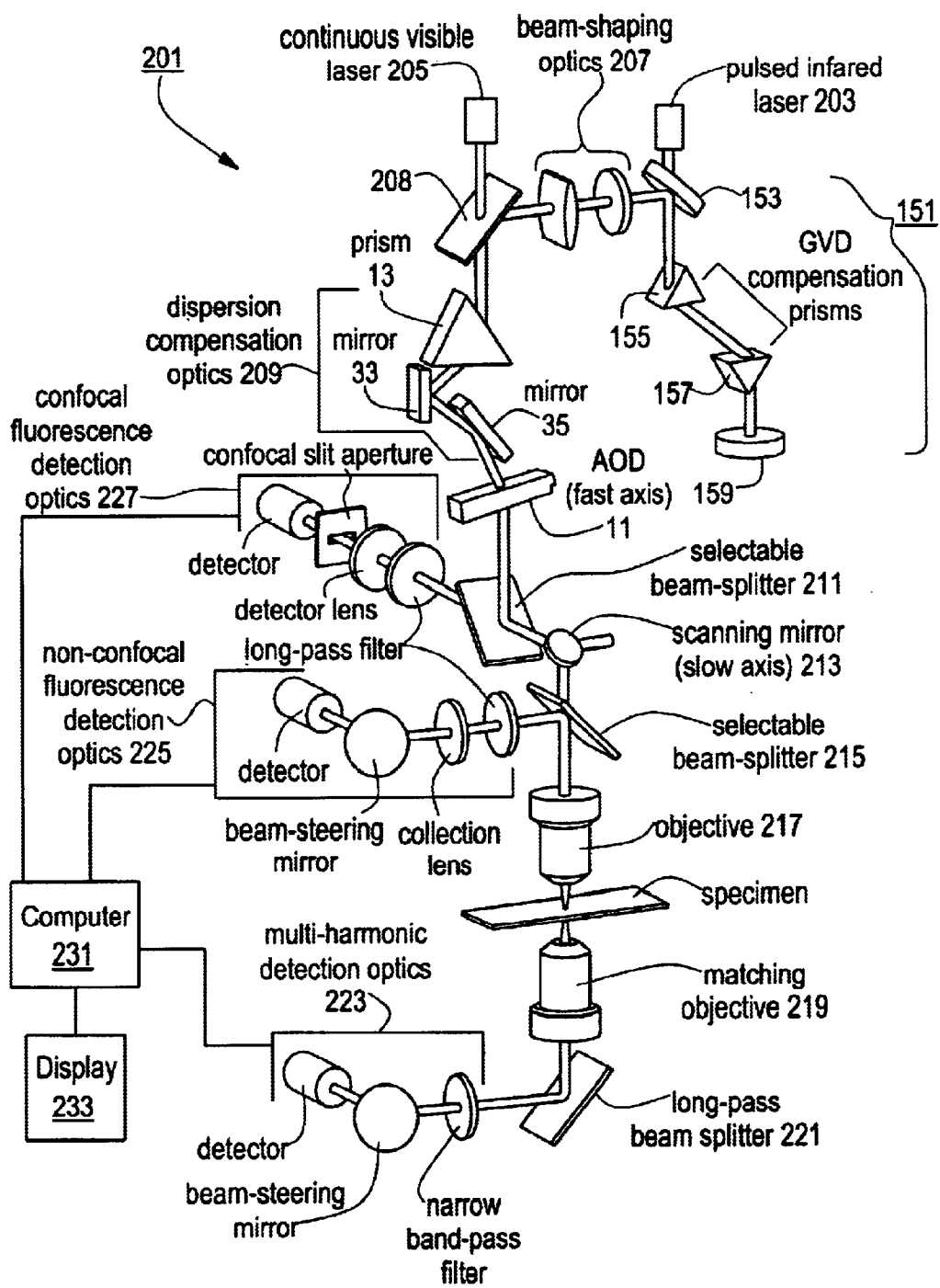
FIG. 11 is a schematic diagram of one embodiment of a laser scanning microscope constructed according to the teachings of the present invention, said laser scanning microscope being capable of operating in a single-photon confocal mode, a multi-photon excited fluorescence mode and a multi-harmonic generation mode.

Referring now to FIG. 11, there is shown a schematic diagram of one embodiment of a laser scanning microscope constructed according to the teachings of the present invention, said laser scanning microscope being represented generally by reference numeral 201.

Microscope 201, which is capable of operating in one or more of a single-photon fluorescence confocal mode, a multi-photon excited fluorescence mode and a multi-harmonic generation mode, comprises two alternative illumination sources, namely, a pulsed infrared laser 203 and a continuous visible laser 205. The output of pulsed infrared laser 203 is optically coupled to group velocity dispersion compensation apparatus 151 whose output, in turn, is coupled to beam-shaping optics 207. The output from beam-shaping optics 207 is then reflected off a beam splitter 208, where it is inputted into dispersion compensation optics 209 comprising prism 13, mirror 33 and mirror 35. (Laser 205 is oriented so that its output is passed through beam splitter 208 to dispersion compensation optics 209.) The output from dispersion compensation optics 209 is then inputted into acousto-optical deflector 11, which scans the beam along one axis.

The scanning beam is then reflected off a selectable beam-splitter 211 onto a scanning mirror 213, which scans the beam along a second axis. The thus twice-scanned beam is then passed through a selectable beam splitter 215 and then brought to focus on a specimen using an objective 217. Light emitted from the specimen in the forward direction is collected by a matching objective 219, reflected off a long-pass beam-splitter 221 and then detected using multi-harmonic detection optics 223. Light emitted from the specimen in a backward direction is passed back through objective 217 and is then split by selectable beam-splitter 215 into a first component that is then detected by non-confocal fluorescence detection optics 225 and a second component that travels back across scanning mirror 213 and through beam-splitter 211 to confocal fluorescence detection optics 227.

The detection signals from multi-harmonic detection optics 223, non-confocal fluorescence detection optics 225 and confocal fluorescence detection optics 227 are then inputted to a computer 231, which uses the detection signals to form an image of the specimen, said image then being displayed on a display 233.

Referring now to FIGS. 12A through 12D, there are shown images of fluorescent pollen grains obtained using laser scanning microscope 201 in a two-photon excited fluorescence mode with 100 fs pulses centered at 900 nm being used for illumination and image acquisition rates of (A) 30 Hz; (B) 120 Hz; (C) 240 Hz; and (D) 480 Hz, respectively (scale bar=20 $\mu$m).

Figure 13A:
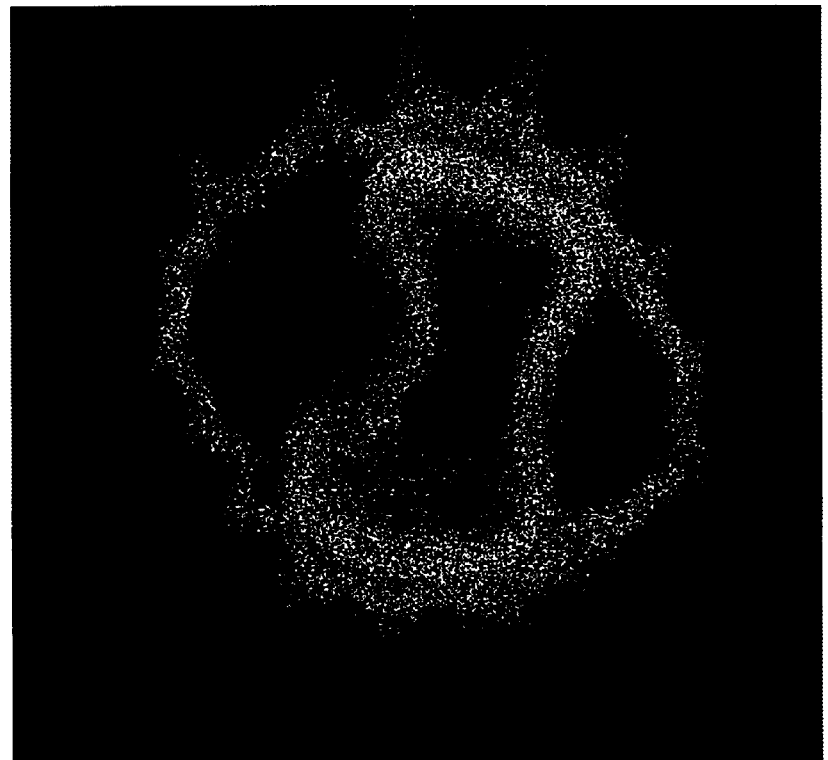
FIGS. 13A and 13B are images of a pair of fluorescent pollen grains obtained using the laser scanning microscope of FIG. 11 in a two-photon excited fluorescence mode, using 1.5 ps pulses centered at 900 nm for illumination and an image acquisition rate of 30 Hz (scale bar=5 $\mu$m)
Figure 13B:
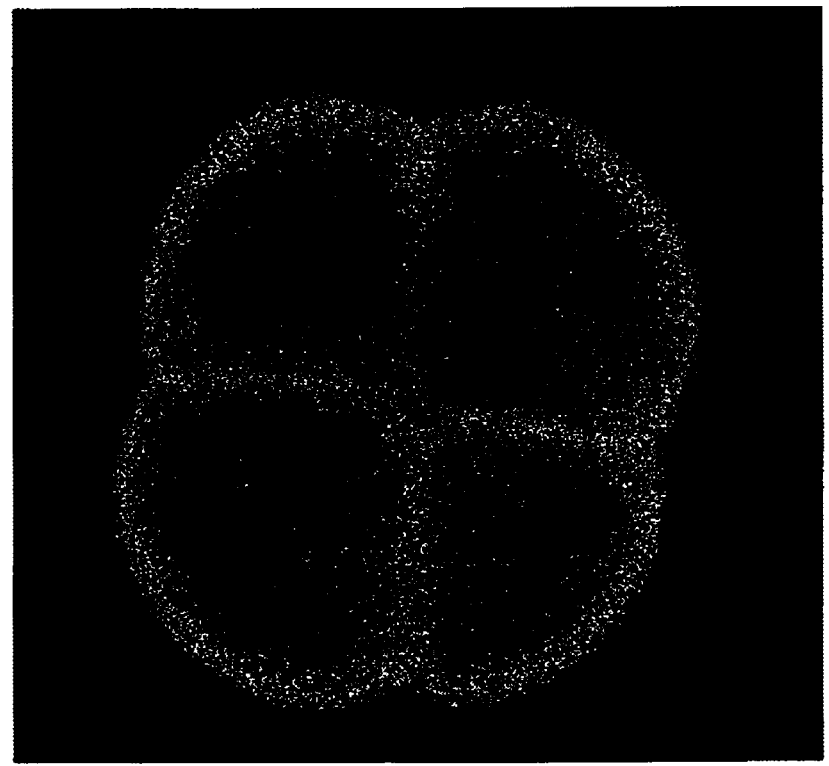

Referring now to FIGS. 13A and 13B, there are shown images of a pair of fluorescent pollen grains obtained using laser scanning microscope 201 in a two-photon excited fluorescence mode with 1.5 ps pulses centered at 900 nm for illumination and an image acquisition rate of 30 Hz (scale bar=5 $\mu$m).

Figure 14:
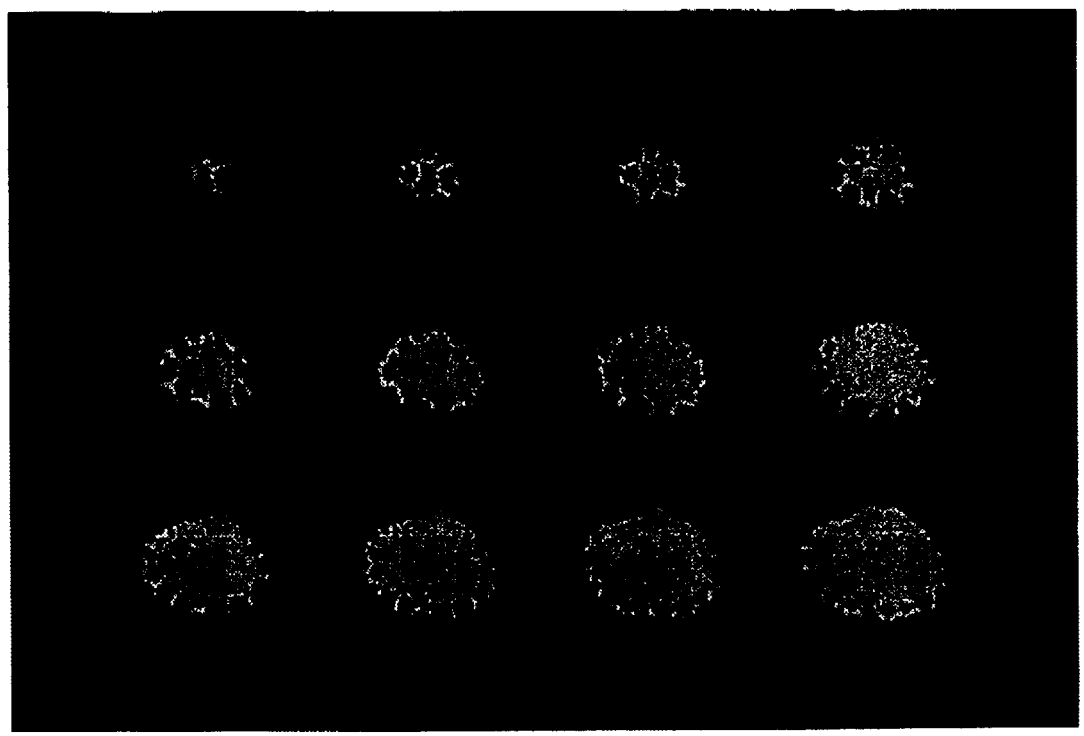
FIG. 14 is a series of sectional images (each image averaged over 32 scans, adjacent images representing sections spaced 2 $\mu$m apart in the vertical axis) of a fluorescent pollen grain obtained using the laser scanning microscope of FIG. 11 in a two-photon excited fluorescence mode, using 1.5 ps pulses centered at 900 nm for illumination and an image acquisition rate of 30 Hz (scale bar=20 $\mu$m)

Referring now to FIG. 14, there is shown a series of sectional images (each image averaged over 32 scans, adjacent images representing sections spaced 2 $\mu$m apart in the vertical axis) of a fluorescent pollen grain obtained using laser scanning microscope 201 in a two-photon excited fluorescence mode with 1.5 ps pulses centered at 900 nm for illumination and an image acquisition rate of 30 Hz (scale bar=20 $\mu$m).

Figure 15:
FIG. 15 is an image of neurons expressing green fluorescent protein from the Dor 47A promoter in the brain of a living fruit fly, *Drosophila melanogaster*, obtained using the laser scanning microscope of FIG. 11 in a two-photon excited fluorescence mode, using 100 fs pulses at 900 nm for illumination at an image acquisition rate of 30 Hz (scale bar=10 $\mu$m)

Referring now to FIG. 15, there is shown an image of neurons expressing green fluorescent protein from the Dor 47A promoter in the brain of a living fruit fly, *Drosophila melanogaster*, said image obtained using laser scanning microscope 201 in a two-photon excited fluorescence mode with 100 fs pulses at 900 nm for illumination at an image acquisition rate of 30 Hz (scale bar=10 $\mu$m).

Figure 16A:
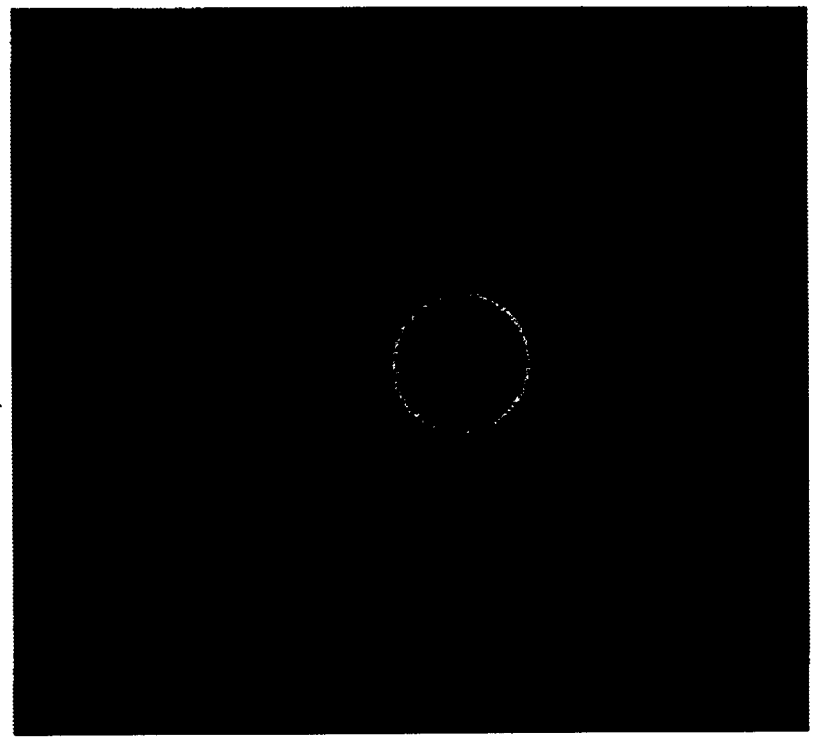
FIGS. 16(a) and 16(b) are images of a CHO cell stained with 10 μM DiA obtained using the laser scanning microscope of FIG. 11 in a two-photon excited fluorescence mode and in a multi-harmonic generation mode, respectively, using 100 fs pulses at 900 nm for illumination.
Figure 16B:

Referring now to FIGS. 16(*a*) and 16(*b*), there are shown images of a CHO cell stained with 10 $\mu$M 4-(4-(dihexadecylamino)styryl)-N-methylpyridinium iodide (commercially available as DiA dye, Molecular Probes, Eugene, Oreg.), said images being obtained using laser scanning microscope 201 in a two-photon excited fluorescence mode and in a multi-harmonic generation mode, respectively, with 100 fs pulses at 900 nm being used for illumination.

Figure 17A:
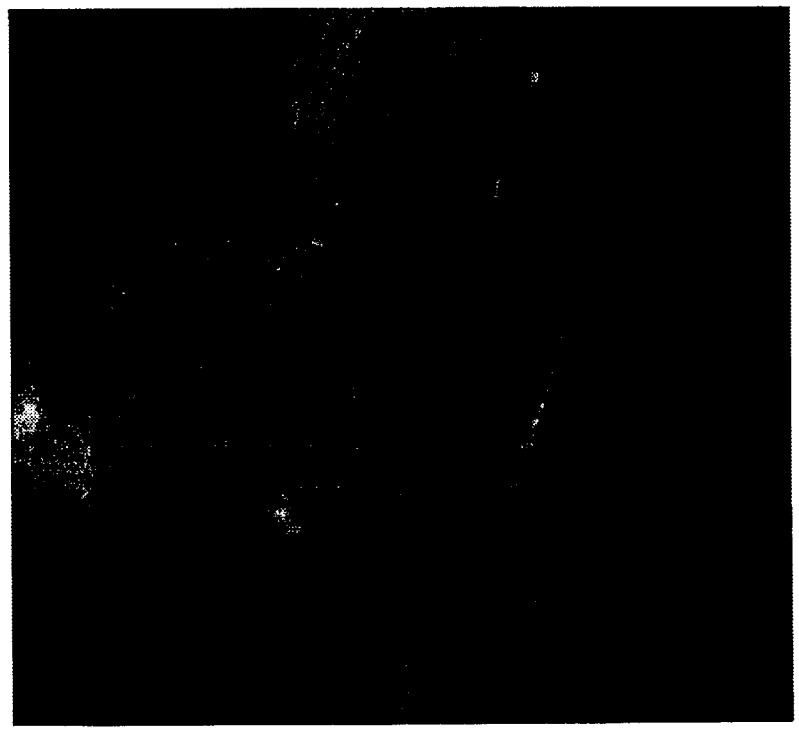
FIGS. 17(a) and 17(b) are images of hippocampal neurons stained with 10 μM FM1-43 obtained using the laser scanning microscope of FIG. 11 in a two-photon excited fluorescence mode and in a multi-harmonic generation mode, respectively, using 100 fs pulses at 900 nm for illumination.
Figure 17B:

Referring now to FIGS. 17(a) and 17(b), there are shown images of hippocampal neurons stained with 10 μM N-(3-triethylammoniumpropyl)-4-(4-(dibutylamino)styryl) pyridinium dibromide (commercially available as FM® 1-43 dye, Molecular Probes, Eugene, Oreg.), said images being obtained using laser scanning microscope 201 in a two-photon excited fluorescence mode and in a multi-harmonic generation mode, respectively, with 100 fs pulses at 900 nm being used for illumination.

Figure 18:
FIG. 18 is a single frame in a series of 300 images, acquired at 30 Hz, of a hippocampal neuron stained with 5 μM Fluo-3 AM ester for 30 minutes, the images being obtained using the laser scanning microscope of FIG. 11 in a two-photon excited fluorescence mode using 100 fs pulses at 900 nm for illumination.

Referring now to FIG. 18, there is shown a single frame in a series of 300 images, acquired at 30 Hz, of a hippocampal neuron stained with 5 μM glycine, N-[4-[6-[(acetyloxy)methoxy]-2,7-dichloro-3-oxo-3H-xanthen-9-yl]-2-[2-[2-[bis [2-[(acetyloxy)methoxy]-2-oxyethyl]amino]-5-methylphenoxy]ethoxy]phenyl]-N-[2-[(acetyloxy)methoxy]-2-oxyethyl]-,(acetyloxy)methyl ester (commercially available as Molecular Probes, Eugene, Oreg.) for 30 minutes, the images being obtained using laser scanning microscope 201 in a two-photon excited fluorescence mode, with 100 fs pulses at 900 nm being used for illumination.

Figure 19:
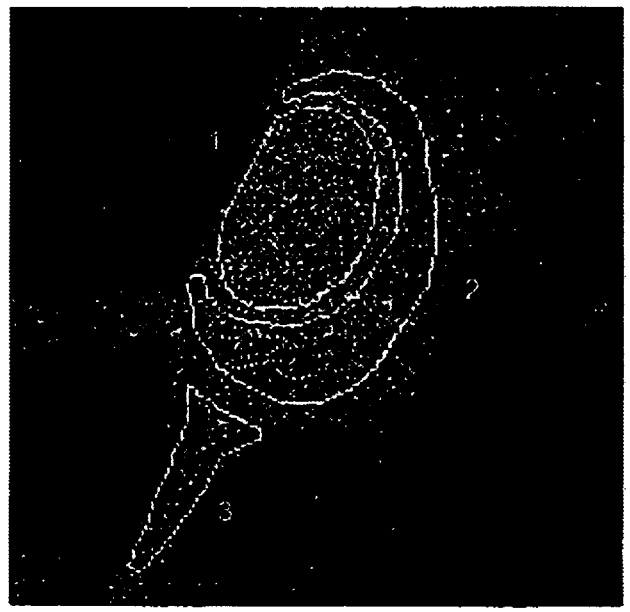
FIG. 19 is an image identifying three regions of interest within the neuron of FIG. 18: (1) the nucleus, (2) the cytoplasm and (3) a dendrite.
Figure 20:
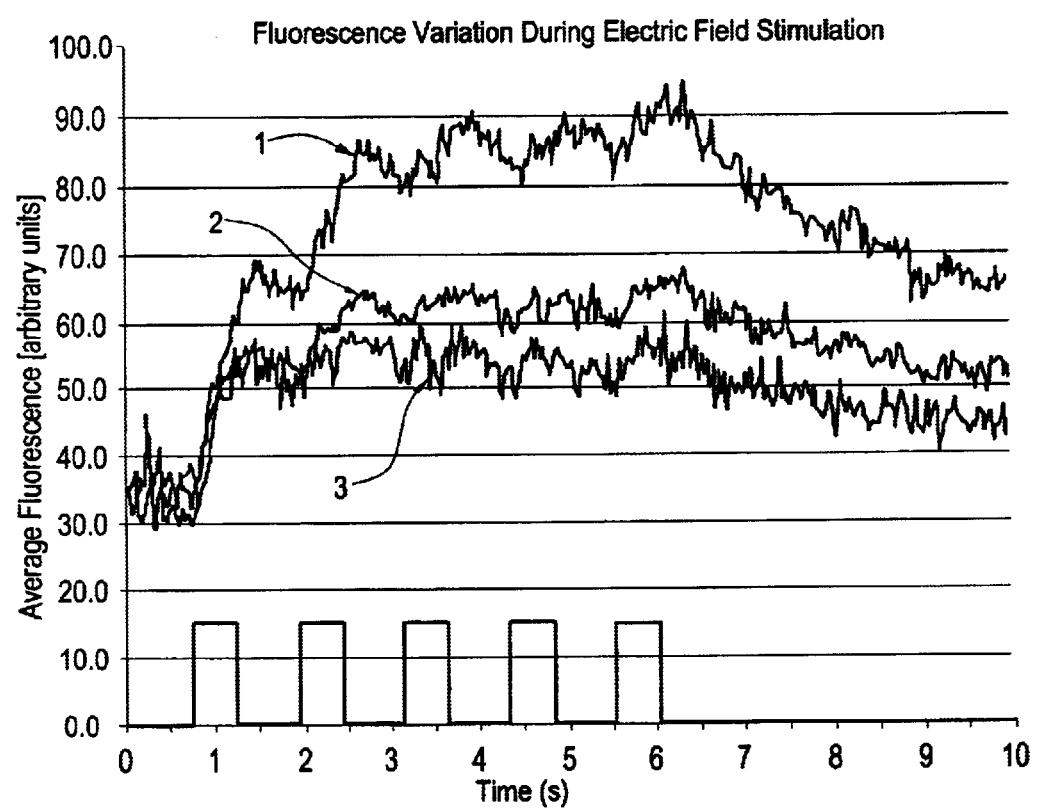
FIG. 20 is a graph showing the average fluorescence intensity in each of the three regions of the neuron of FIG. 18 during electric field stimulation consisting of five 500 ms trains, each such train containing twelve 2 ms pulses of 30 V/cm.

Referring now to FIG. 19, there is shown an image identifying three regions of interest within the neuron of FIG. 18: (1) the nucleus, (2) the cytoplasm and (3) a dendrite. FIG. 20 is a graph showing the average fluorescence intensity in each of the three regions of the neuron of FIG. 18 during electric field stimulation consisting of five 500 ms trains, each such train containing twelve 2 ms pulses of 30 V/cm.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. An apparatus for steering a beam of light, said apparatus comprising:
    (a) an acousto-optical deflector; and
    (b) a spectrally dispersive element positioned in front of said acousto-optical deflector, said spectrally dispersive element and said acousto-optical deflector being optically coupled to one another, said spectrally dispersive element being oriented relative to said acousto-optical deflector so that said spectrally dispersive element disperses multi-chromatic light in a direction opposite to that dispersed by said acousto-optical deflector.

2. The apparatus as claimed in claim 1 wherein said spectrally dispersive element is constructed to disperse multi-chromatic light in an amount equally opposite to, for at least a portion of said multi-chromatic light, that dispersed by said acousto-optical deflector.

3. The apparatus as claimed in claim 1 wherein said spectrally dispersive element is selected from the group consisting of a prism, a grating and a second acousto-optical deflector.

4. The apparatus as claimed in claim 3 wherein said spectrally dispersive element is a prism.

5. An apparatus for steering a beam of light, said apparatus comprising:
    (a) an acousto-optical deflector;
    (b) a spectrally dispersive element, said spectrally dispersive element and said acousto-optical deflector being optically coupled to one another, wherein said spectrally dispersive element is positioned in front of said acousto-optical deflector and is oriented relative to said acousto-optical deflector so that said spectrally dispersive element disperses multi-chromatic light in a direction opposite to that dispersed by said acousto-optical deflector, said spectrally dispersive element being constructed to disperse multi-chromatic light in an amount equally opposite to, for at least a portion of said multi-chromatic light, that dispersed by said acousto-optical deflector; and
    (c) a rotatable mirror, said rotatable mirror being optically coupled to each of said acousto-optical deflector and said spectrally dispersive element and being positioned therebetween.

6. The apparatus as claimed in claim 5 further comprising a fixed mirror, said fixed mirror being optically coupled to each of said acousto-optical deflector, said rotatable mirror and said spectrally dispersive element and being positioned between said acousto-optical deflector and said spectrally dispersive element.

7. The apparatus as claimed in claim 5 further comprising means for rotating said rotatable mirror.

8. The apparatus as claimed in claim 7 wherein said rotating means comprises a rotatably mounted arm and a motor for rotating said rotatably mounted arm, said rotatable mirror being fixedly mounted on said rotatably mounted arm.

9. The apparatus as claimed in claim 8 wherein said motor is controllable by computer.

10. The apparatus as claimed in claim 9 further comprising a base, said spectrally dispersive element, said rotatable mirror, said rotatably mounted arm and said motor being mounted on said base.

11. An apparatus for steering a beam of light, said apparatus comprising:
    (a) an acousto-optical deflector;
    (b) a spectrally dispersive element, said spectrally dispersive element and said acousto-optical deflector being optically coupled to one another, wherein said spectrally dispersive element is positioned in front of said acousto-optical deflector and is oriented relative to said acousto-optical deflector so that said spectrally dispersive element disperses multi-chromatic light in a direction opposite to that dispersed by said acousto-optical deflector, said spectrally dispersive element being constructed to disperse multi-chromatic light in an amount equally opposite to, for at least a portion of said multi-chromatic light, that dispersed by said acousto-optical deflector; and
    (c) a rotatable mirror, said rotatable mirror being optically coupled to said spectrally dispersive element and being positioned in front thereof.

12. The apparatus as claimed in claim 11 further comprising means for rotating said rotatable mirror.

13. The apparatus as claimed in claim 12 wherein said rotating means comprises a rotatably mounted arm and a motor for rotating said rotatably mounted arm, said rotatable mirror being fixedly mounted on said rotatably mounted arm.

14. The apparatus as claimed in claim 13 wherein said motor is controllable by computer.

15. The apparatus as claimed in claim 14 further comprising a base, said spectrally dispersive element, said rotatable mirror, said rotatably mounted arm and said motor being mounted on said base.

16. An apparatus for steering a beam of light, said apparatus comprising:
(a) an acousto-optical deflector;
(b) a spectrally dispersive element, said spectrally dispersive element and said acousto-optical deflector being optically coupled to one another, wherein said spectrally dispersive element is positioned behind said acousto-optical deflector is oriented relative to said acousto-optical deflector so that said spectrally dispersive element disperses multi-chromatic light in a direction opposite to that dispersed by said acousto-optical deflector, said spectrally dispersive element being constructed to disperse multi-chromatic light in an amount equally opposite to, for at least a portion of said multi-chromatic light, that dispersed by said acousto-optical deflector; and
(c) a rotatable mirror, said rotatable mirror being optically coupled to each of said acousto-optical deflector and said spectrally dispersive element and being positioned therebetween.

17. The apparatus as claimed in claim 16 further comprising means for rotating said rotatable mirror.

18. The apparatus as claimed in claim 17 wherein said rotating means comprises a rotatably mounted arm and a motor for rotating said rotatably mounted arm, said rotatable mirror being fixedly mounted on said rotatably mounted arm.

19. The apparatus as claimed in claim 18 wherein said motor is controllable by computer.

20. The apparatus as claimed in claim 19 further comprising a base, said spectrally dispersive element, said rotatable mirror, said rotatably mounted arm and said motor being mounted on said base.

21. An apparatus for steering a beam of light, said apparatus comprising:
(a) first beam deflection means for deflecting said beam along a first axis, said first beam deflection means comprising
(i) a first acousto-optical deflector, and
(ii) a first spectrally dispersive element positioned in front of said acousto-optical deflector, said first spectrally dispersive element and said first acousto-optical deflector being optically coupled to one another, said first spectrally dispersive element being oriented relative to said first acousto-optical deflector so that said first spectrally dispersive element disperses multi-chromatic light in a direction opposite to that dispersed by said first acousto-optical deflector, said first spectrally dispersive element being constructed to disperse multi-chromatic light, for at least a portion of said multi-chromatic light, in an amount equal to that dispersed by said first acousto-optical deflector; and
(b) second beam deflection means for deflecting said beam along a second axis, said second axis being different from said first axis, said second beam deflection means comprising
(i) a second acousto-optical deflector, and
(ii) a second spectrally dispersive element, said second spectrally dispersive element and said second acousto-optical deflector being optically coupled to one another, said second spectrally dispersive element being oriented relative to said second acousto-optical deflector so that said second spectrally dispersive element disperses multi-chromatic light in a direction opposite to that dispersed by said second acousto-optical deflector, said second spectrally dispersive element being constructed to disperse multi-chromatic light, for at least a portion of said multi-chromatic light, in an amount equal to that dispersed by said second acousto-optical deflector.

22. The apparatus as claimed in claim 21 wherein said second axis is perpendicular to said first axis.

23. The apparatus as claimed in claim 21 wherein said first beam deflection means is constructed to scan said beam over a plurality of contiguous locations along said first axis and wherein said second beam deflection means is constructed to scan said beam over a plurality of contiguous locations along said second axis.

24. An apparatus for steering a beam of light, said apparatus comprising:
(a) first beam deflection means for deflecting said beam along a first axis, said first beam deflection means comprising:
(i) a first acousto-optical deflector, and
(ii) a first spectrally dispersive element, said first spectrally dispersive element and said first acousto-optical deflector being optically coupled to one another, said first spectrally dispersive element being oriented relative to said first acousto-optical deflector so that said first spectrally dispersive element disperses multi-chromatic light in a direction opposite to that dispersed by said first acousto-optical deflector, said first spectrally dispersive element being constructed to disperse multi-chromatic light, for at least a portion of said multi-chromatic light, in an amount equal to that dispersed by said first acousto-optical deflector; and
(b) second beam deflection means for deflecting said beam along a second axis, said second axis being different from said first axis, said second beam deflection means comprising
(i) a second acousto-optical deflector, and
(ii) a second spectrally dispersive element, said second spectrally dispersive element and said second acousto-optical deflector being optically coupled to one another, said second spectrally dispersive element being oriented relative to said second acousto-optical deflector so that said second spectrally dispersive element disperses multi-chromatic light in a direction opposite to that dispersed by said second acousto-optical deflector, said second spectrally dispersive element being constructed to disperse multi-chromatic light, for at least a portion of said multi-chromatic light, in an amount equal to that dispersed by said second acousto-optical deflector; and
(c) wherein said first beam deflection means is constructed to scan said beam over a plurality of non-contiguous locations long along said first axis and wherein said second beam deflection means is constructed to randomly deflect said beam over a plurality of contiguous locations along said second axis.

25. A method of steering a beam of light, said method comprising the steps of:
(a) providing a beam of light;
(b) then, passing said beam of light through a spectrally dispersive element; and
(c) then, deflecting said beam of light using an acousto-optical deflector;
(d) wherein said spectrally dispersive element is oriented to disperse multi-chromatic light in a direction opposite to that dispersed by said acousto-optical deflector.

26. The method as claimed in claim 25 wherein said spectrally dispersive element is constructed to disperse multi-chromatic light, for at least a portion of said multi-chromatic light, in an amount equal to that dispersed by said acousto-optical deflector.

27. The method as claimed in claim 25 wherein said beam of light is a continuous beam of light.

28. The method as claimed in claim 25 wherein said beam of light is a pulsed beam of light.

29. The method as claimed in claim 25 wherein said beam of light is a beam of ultrashort light pulses.

30. The method as claimed in claim 29 wherein said ultrashort light pulses have a pulse duration of less than one picosecond.

31. The method as claimed in claim 29 wherein said ultrashort light pulses have a pulse duration of greater than or equal to one picosecond.

32. The method as claimed in claim 25 wherein said beam of light is a beam of ultrashort multi-chromatic laser light pulses having a bandwidth of no more than about 40 nm.

33. The method as claimed in claim 25 wherein said light has a wavelength in the range of about 400 to 1000 nm.

34. The method as claimed in claim 33 wherein said light has a wavelength in the range of about 400 to 700 nm.

35. The method as claimed in claim 33 wherein said light has a wavelength in the range of about 700 to 1000 nm.

36. The method as claimed in claim 25 wherein said spectrally dispersive element is a prism.

37. A method of imaging a sample using multi-photon excited fluorescence laser scanning microscopy, said method comprising the steps of:
 (a) providing a sample containing fluorescent molecules which radiate photons of a first characteristic energy;
 (b) producing a scanning beam of ultrashort laser light pulses, said scanning beam producing step comprising
  (i) providing a beam of ultrashort laser light pulses comprising photons of a second characteristic energy, wherein said second characteristic energy is less than said first characteristic energy and wherein the simultaneous absorption of a plurality of said photons of said second characteristic energy by said fluorescent molecules causes the fluorescence of said fluorescent molecules,
  (ii) passing said beam through a spectrally dispersive element, and
  (iii) deflecting said beam using an acousto-optical deflector,
  (iv) wherein said step of passing said beam through a spectrally dispersive element is performed prior to the step of deflecting said beam using an acousto-optical deflector and wherein said spectrally dispersive element is oriented to disperse multi-chromatic light in a direction opposite to that dispersed by said acousto-optical deflector;
 (c) focusing said scanning beam at a focal point within said sample to produce an illumination intensity sufficiently high only at said focal point to produce molecular excitation and fluorescence of said sample by simultaneous absorption of a plurality of incident photons;
 (d) detecting the fluorescence produced by said sample; and
 (e) using the detected fluorescence to form an image of the sample.

38. The method as claimed in claim 37 wherein said spectrally dispersive element is constructed to disperse multi-chromatic light, for at least a portion of said multi-chromatic light, in an amount equal to that dispersed by said acousto-optical deflector.

39. A multi-photon excited fluorescence laser scanning microscope for forming a magnified image of a sample, said sample containing fluorescent molecules which radiate photons of a first characteristic energy, said multi-photon excited fluorescence laser scanning microscope comprising:
 (a) means for producing a scanning beam of ultrashort laser light pulses, said scanning beam producing means comprising
  (i) a laser source for providing a beam of ultrashort laser light pulses comprising photons of a second characteristic energy, wherein said second characteristic energy is less than said first characteristic energy and wherein the simultaneous absorption of a plurality of said photons of said second characteristic energy by said fluorescent molecules causes the fluorescence of said fluorescent molecules,
  (ii) a first acousto-optical deflector optically coupled to said laser source for scanning said beam along a first axis,
  (iii) a first spectrally dispersive element positioned in front of said first acousto-optical deflector and optically coupled to said first acousto-optical deflector, said first spectrally dispersive element being oriented relative to said first acousto-optical deflector so as to disperse multi-chromatic light in a direction opposite to that dispersed by said first acousto-optical deflector,
 (b) means for focusing said scanning beam to a focal point within said sample to produce an illumination intensity sufficiently high only at said focal point to produce molecular excitation and fluorescence of said sample by simultaneous absorption of at least two incident photons;
 (c) means for detecting the fluorescence produced by said sample; and
 (d) means for using the detected fluorescence to form a magnified image of the sample.

40. The multi-photon excited fluorescence laser scanning microscope as claimed in claim 39 wherein said first spectrally dispersive element is constructed to disperse multi-chromatic light, for at least a portion of said multi-chromatic light, in an amount equal to that dispersed by said first acousto-optical deflector.

41. The multi-photon excited fluorescence laser scanning microscope as claimed in claim 39 wherein said scanning beam producing means further comprises means for scanning the sample in a direction perpendicular to said first axis.

42. The multi-photon laser scanning microscope as claimed in claim 41 wherein said means for scanning the sample in a direction perpendicular to said first axis comprises a second acousto-optical deflector and a second spectrally dispersive element, said second spectrally dispersive element being oriented relative to said second acousto-optical deflector so as to disperse multi-chromatic light in a direction opposite to that dispersed by said second acousto-optical deflector.

43. A laser scanning microscope for forming a magnified image of a sample, the sample containing fluorophores, said laser scanning microscope comprising:
 (a) means for producing a scanning beam of light pulses, said scanning beam producing means comprising:
  (i) means for providing a beam of light pulses, said light pulses being of a wavelength suitable to excite said fluorophores, (ii) a first acousto-optical deflector optically coupled to said beam providing means for scanning said beam along a first axis, (iii) a first spectrally dispersive element optically coupled to said first acousto-optical deflector, said first spectrally dispersive element being oriented relative to said first acousto-optical deflector so as to disperse multi-chromatic light in a direction opposite to that dispersed by said first acousto-optical deflector, said first spectrally dispersive element being positioned between said beam providing means and said first acousto-optical deflector;

(b) means for focusing said scanning beam to a focal point within said sample;

(c) means for detecting the fluorescence produced by said sample; and (d) means for using the detected fluorescence to form a magnified image of the sample.

44. A method of imaging a sample using multi-harmonic generation laser scanning microscopy, said method comprising the steps of:

(a) providing a sample, the sample containing molecules having the appropriate nonlinear susceptibility;

(b) producing a scanning beam of ultrashort laser light pulses, said scanning beam producing step comprising
  (i) providing a beam of ultrashort laser light pulses comprising photons of a first wavelength capable of interacting with said molecules having the appropriate nonlinear susceptibility to create, by multi-harmonic generation, photons of a second wavelength,
  (ii) passing said beam through a spectrally dispersive element, and
  (iii) deflecting said beam using an acousto-optical deflector,
  (iv) wherein said spectrally dispersive element is oriented to disperse multi-chromatic light in a direction opposite to that dispersed by said acousto-optical deflector;

(c) focusing said scanning beam at a focal point within said sample to produce an illumination intensity sufficiently high only at said focal point to generate, by multi-harmonic generation, photons of said second wavelength;

(d) detecting the photons of said second wavelength emitted from said sample; and (e) using the detected photons of said second wavelength to form an image of the sample.

45. A method of imaging a sample using multi-harmonic generation laser scanning microscopy, said method comprising the steps of:

(a) providing a sample, the sample containing molecules having the appropriate nonlinear susceptibility;

(b) producing a scanning beam of ultrashort laser light pulses, said scanning beam producing step comprising
  (i) providing a beam of ultrashort laser light pulses comprising photons of a first wavelength capable of interacting with said molecules having the appropriate nonlinear susceptibility to create, by multi-harmonic generation, photons of a second wavelength,
  (ii) passing said beam through a spectrally dispersive element, and
  (iii) deflecting said beam using an acousto-optical deflector,
  (iv) wherein said spectrally dispersive element is oriented to disperse multi-chromatic light in a direction opposite to that dispersed by said acousto-optical deflector and wherein said step of passing said beam through a spectrally dispersive element is performed prior to said step of deflecting said beam using an acousto-optical deflector;

(c) focusing said scanning beam at a focal point within said sample to produce an illumination intensity sufficiently high only at said focal point to generate, by multi-harmonic generation, photons of said second wavelength;

(d) detecting the photons of said second wavelength emitted from said sample; and (e) using the detected photons of said second wavelength to form an image of the sample.

46. A multi-harmonic generation laser scanning microscope for forming a magnified image of a sample, the sample containing molecules having the appropriate nonlinear susceptibility, said multi-harmonic generation laser scanning microscope comprising:

(a) means for producing a scanning beam of ultrashort laser light pulses, said scanning beam producing means comprising
  (i) a laser source for providing a beam of ultrashort light pulses comprising photons of a first wavelength capable of interacting with said molecules having the appropriate nonlinear susceptibility to create, by multi-harmonic generation, photons of a second wavelength,
  (ii) a first acousto-optical deflector optically coupled to said laser source for scanning said beam along a first axis,
  (iii) a first spectrally dispersive element positioned in front of said first acousto-optical deflector and optically coupled to said first acousto-optical deflector, said first spectrally dispersive element being oriented relative to said first acousto-optical deflector so as to disperse multi-chromatic light in a direction opposite to that dispersed by said first acousto-optical deflector;

(b) means for focusing said scanning beam at a focal point within said sample to produce an illumination intensity sufficiently high only at said focal point to generate, by multi-harmonic generation, photons of said second wavelength;

(c) means for detecting the photons of said second wavelength emitted from said sample; and (d) means for using the detected photons of said second wavelength to form an image of the sample.

47. A laser scanning microscope, said laser scanning microscope comprising:

(a) means for producing a scanning beam of laser light, said scanning beam producing means comprising
  (i) a laser source for providing a beam of laser light,
  (ii) a first acousto-optical deflector optically coupled to said laser source for scanning said beam along a first axis,
  (iii) a first spectrally dispersive element positioned in front of said first acousto-optical deflector and optically coupled to said first acousto-optical deflector, said first spectrally dispersive element being oriented relative to said first acousto-optical deflector so as to disperse multi-chromatic light in a direction opposite to that dispersed by said first acousto-optical deflector;

(b) means for focusing said scanning beam at a focal point within a sample;

(c) confocal fluorescence detection means for detecting single-photon fluorescence emitted from said sample;

(d) non-confocal fluorescence detection means for detecting multi-photon fluorescence emitted from said sample;

(e) multi-harmonic generation detection means for detecting multi-harmonic generation photons emitted from said sample; and (f) means, coupled to said confocal fluorescence detection means, said non-confocal detection means and said multi-harmonic generation detection means, for forming an image of said sample using at least one of the detected single-photon fluorescence, the detected multi-photon fluorescence and the detected multi-harmonic generation photons.

48. An apparatus for steering a beam of light, said apparatus comprising:

(a) first beam deflection means for deflecting said beam along a first axis, said first beam deflection means comprising
  (i) a first acousto-optical deflector, and
  (ii) a first spectrally dispersive element, said first spectrally dispersive element and said first acousto-optical deflector being optically coupled to one another, said first spectrally dispersive element being oriented relative to said first acousto-optical deflector so that said first spectrally dispersive element disperses multi-chromatic light in a direction opposite to that dispersed by said first acousto-optical deflector, said first spectrally dispersive element being constructed to disperse multi-chromatic light, for at least a portion of said multi-chromatic light, in an amount equal to that dispersed by said first acousto-optical deflector; and (b) second beam deflection means for deflecting said beam along a second axis, said second axis being different from said first axis, said second beam deflection means comprising
  (i) a second acousto-optical deflector, and
  (ii) a second spectrally dispersive element, said second spectrally dispersive element and said second acousto-optical deflector being optically coupled to one another, said second spectrally dispersive element being oriented relative to said second acousto-optical deflector so that said second spectrally dispersive element disperses multi-chromatic light in a direction opposite to that dispersed by said second acousto-optical deflector, said second spectrally dispersive element being constructed to disperse multi-chromatic light, for at least a portion of said multi-chromatic light, in an amount equal to that dispersed by said second acousto-optical deflector; and (c) wherein at least one of said first beam deflection means and said second beam deflection means is constructed to scan said beam over a plurality of non-contiguous locations.

49. The apparatus as claimed in claim 48 wherein both said first beam deflection means and said second beam deflection means are constructed to scan said beani over a plurality of non-contiguous locations.

* * * * *